United States Patent
Kheradvar et al.

(10) Patent No.: US 11,701,227 B2
(45) Date of Patent: Jul. 18, 2023

(54) DELIVERY SYSTEM FOR TRANSCATHETER VALVES

(71) Applicant: The Regents of the University of California, Oakland, CA (US)

(72) Inventors: Arash Kheradvar, Irvine, CA (US); Gregory Scott Kelley, Santee, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 431 days.

(21) Appl. No.: 16/866,913

(22) Filed: May 5, 2020

(65) Prior Publication Data
US 2020/0352717 A1    Nov. 12, 2020

Related U.S. Application Data

(60) Provisional application No. 62/843,970, filed on May 6, 2019.

(51) Int. Cl.
*A61F 2/24*      (2006.01)
*A61F 2/95*      (2013.01)

(52) U.S. Cl.
CPC .......... *A61F 2/2439* (2013.01); *A61F 2/2418* (2013.01); *A61F 2/2436* (2013.01); *A61F 2/95* (2013.01); *A61F 2/9517* (2020.05)

(58) Field of Classification Search
CPC .... A61F 2/2439; A61F 2/2418; A61F 2/2436; A61F 2/9517; A61F 2/95
See application file for complete search history.

(56) References Cited

U.S. PATENT DOCUMENTS

| | | | |
|---|---|---|---|
| 9,668,859 B2 | 6/2017 | Kheradvar et al. | |
| 9,744,037 B2 | 8/2017 | Kheradvar et al. | |
| 2013/0150716 A1* | 6/2013 | Stigall | A61B 17/3207 600/478 |
| 2014/0277414 A1 | 9/2014 | Kheradvar | |
| 2016/0331566 A1 | 11/2016 | Kheradvar et al. | |
| 2018/0207010 A1 | 7/2018 | Kheradvar et al. | |
| 2019/0083747 A1* | 3/2019 | Khuu | A61M 25/0136 |
| 2019/0133764 A1 | 5/2019 | Carr et al. | |
| 2019/0282360 A1 | 9/2019 | Colavito et al. | |

\* cited by examiner

*Primary Examiner* — Javier G Blanco
(74) *Attorney, Agent, or Firm* — Nguyen Tarbet LLC

(57) ABSTRACT

A gimbal handle assembly including: an inner gimbal and an outer gimbal that are concentrically linked and have pivot axes that are orthogonal relative to each other, a spool coupled to and rotatable around the outer gimbal, and a plurality of draw lines attached to the spool in a circumferential configuration, wherein rotation of the spool and/or rotation of the spool and the outer and inner gimbals increases or reduces tension in the draw lines. Also disclosed are a transcatheter valve delivery assembly that includes the gimbal handle assembly, a multi-lumen catheter, a sleeve attached to a distal end of the multi-lumen catheter, and a transcatheter heart valve including an expandable valve frame. Methods of delivering the transcatheter valve to a subject are described, wherein pitch and yaw orientations of the transcatheter valve can be precisely controlled with enhanced degrees of freedom.

14 Claims, 19 Drawing Sheets

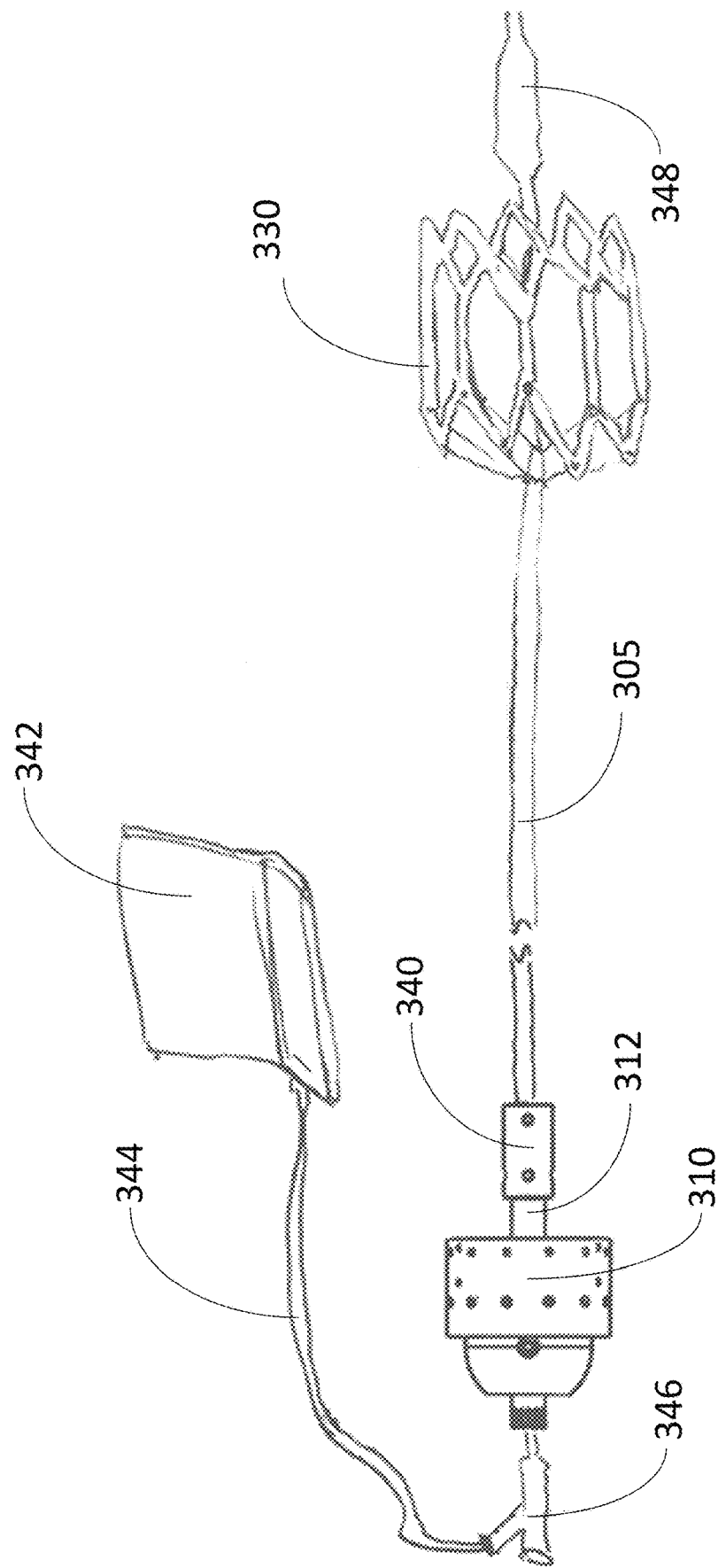

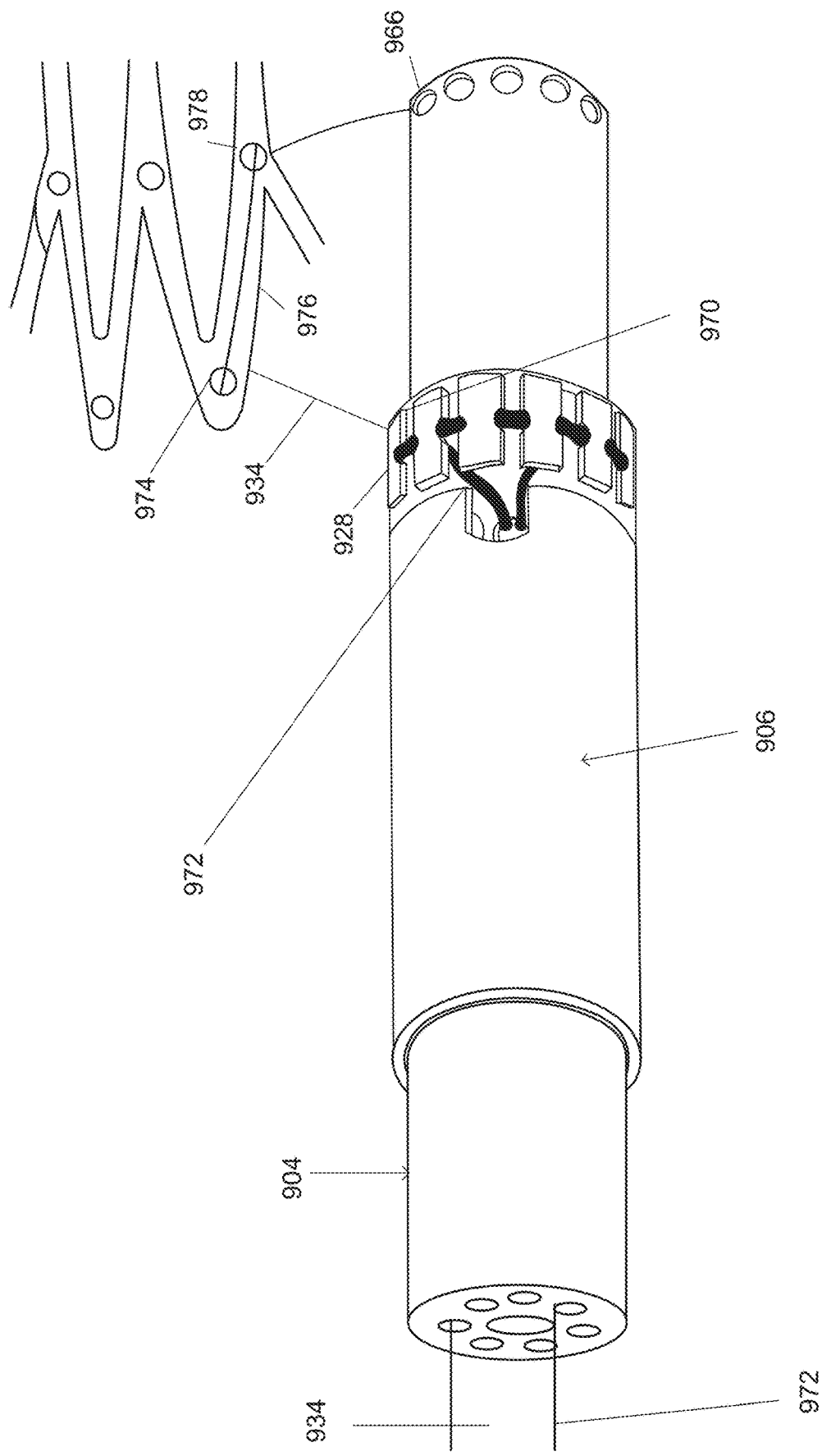

DELIVERY SYSTEM FOR TRANSCATHETER VALVES

STATEMENT REGARDING FEDERALLY SPONSORED R&D

This invention was made with government support under Grant No. IR21EB021513-01 awarded by The National Institutes of Health. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

A delivery system for delivery, deployment and implantation of transcatheter valves comprising a gimbal handle that provides enhanced manipulability of a valve during implantation or retrieval and a slotted restraining ring external to a valve delivery catheter for attachment of draw lines outside of that delivery catheter.

Description of the Related Art

Correct valve positioning is crucial for treatment success and optimal outcomes after transcatheter valve implantation. For example, to maintain a stable and correct lengthwise position with respect to the aortic annulus, a stepwise deployment that allows the valve to be repositioned both circumferentially and in the axial direction (i.e., towards the left ventricle (LV) or the ascending aorta) is important.

Most of the current technologies are limited by instant deployment, and once the valve is deployed, repositioning and/or percutaneous retrieval is not possible, or at least difficult or potentially problematic. Placement of a stented valve in a position that is too high (or proximal) can totally or partially obstruct the coronary ostia in a case of aortic implantation, which may result in myocardial infarction or ischemia. Additionally, if the valve is placed too high in the aorta, it may embolize into the aorta causing significant paravalvular regurgitation. On the other hand, implantation in a position that is too low (or distal) is accompanied by compression of the atrioventricular (AV) node in the membranous septum, which leads to conduction abnormalities.

Further technical developments focusing on enhanced positioning, repositioning, and/or a percutaneously retrievable valve design would facilitate optimal placement, significantly reducing the risk of paravalvular aortic regurgitation, myocardial infarction, or ischemia related to improper positioning.

SUMMARY OF THE INVENTION

The system disclosed herein provides robust control and procedural accuracy for the operator in the delivery, deployment and implantation of transcatheter heart valves. The system may enable repositioning and retrieval of the percutaneously implanted heart valves. A key aspect relates to a gimbal handle that may be used to remotely precisely control expansion/contraction, position and orientation of an expandable transcatheter valve during a surgical procedure. The gimbal handle is connected to multiple draw lines that are releasably coupled to the circumference of a valve frame of the transcatheter valve via a multi-lumen catheter. The gimbal handle may be used to evenly release or retract all draw lines that pass through the multi-lumen catheter to expand or contract an expandable valve from a collapsed state to an expanded state. The gimbal handle may also be used to generate and control differential tension in the multiple draw lines to precisely tilt the transcatheter valve with regard to pitch and yaw movements (tilting the valve in polar and azimuthal directions with respect to longitudinal axis of the distal end of the catheter) or to laterally displace the transcatheter valve relative to the multi-lumen catheter, so that optimal placement of the transcatheter valve is readily achieved.

Some embodiments relate to a transcatheter valve delivery assembly including:
 a gimbal handle,
 a multi-lumen catheter, and
 a valve comprising a valve frame,
 wherein the valve frame is operably coupled to the gimbal handle through the multi-lumen catheter.

In some examples, the gimbal handle includes:
 an inner gimbal and an outer gimbal that are concentrically linked and have pivot axes that are orthogonal relative to each other, wherein the outer gimbal is coupled to the inner gimbal by a first rotatable joint with a first pivot axis that is orthogonal to a longitudinal axis of an elongate member of the gimbal handle assembly, wherein the outer gimbal can pivot around the first pivot axis, and wherein the inner gimbal is coupled to the elongate member by a second rotatable joint with a second pivot axis that is orthogonal to both the first pivot axis and the longitudinal axis of the elongate member, wherein the elongate member and both outer and inner gimbals can pivot around the second pivot axis,
 a spool coupled to and rotatable around the outer gimbal, wherein the outer gimbal is rotatably coupled to the elongate member such that the outer gimbal, and the spool coupled to it can be tilted in an arbitrary direction with respect to the longitudinal axis of the elongate member, and
 a plurality of draw lines, the proximal ends of which are attached to the spool in a circumferential configuration, wherein the draw lines pass through apertures or channels in the spool and then through apertures or channels in the outer gimbal such that rotation of the spool causes the draw lines to wrap around the spool and increase tension in the draw lines.

In some examples:
 rotation of the spool and the outer gimbal around the first rotational joint introduces differential increases in tension of some of the plurality of draw lines and differential reduction in tension of other of the plurality of draw lines, thereby rotating an object circumferentially connected to distal ends of the plurality of draw lines around a first axis, and
 rotation of the spool, outer gimbal and inner gimbal around the second rotatable joint introduces differential increases in tension of some of the plurality of draw lines and differential reduction in tension of other of the plurality of draw lines, thereby rotating the object circumferentially connected to distal ends of the plurality of draw lines around a second axis that is orthogonal to the first axis.

In some examples, tilt angles of the spool/outer gimbal relative to the longitudinal axis of the elongate member may be changed by up to ±60° upon rotation of the spool and outer gimbal around the longitudinal axis of the elongate member.

In some examples, the plurality of draw lines comprises at least three draw lines.

In some examples, the transcatheter valve delivery assembly further includes a slide lock that locks the inner gimbal, the outer gimbal and the elongate member together in a neutral position, wherein none of the gimbals or the spool can tilt in any direction with respect to the longitudinal axis of the elongate member, but the spool can rotate around the outer gimbal, wherein rotation of the spool around the outer gimbal uniformly increases or decreases tension in the plurality of draw lines.

In some examples, the transcatheter valve delivery assembly further includes a sleeve attached to a distal end of the multi-lumen catheter, wherein the gimbal handle assembly is operably linked to the multi-lumen catheter and the sleeve and wherein the valve frame of the transcatheter valve is operably linked to the gimbal handle assembly through the multi-lumen catheter and sleeve by the plurality of draw lines.

In some examples, the transcatheter valve delivery assembly further includes a catheter sheath that is capable of being slid along the longitudinal axis of the sleeve, wherein the catheter sheath may cover the transcatheter valve in a first position, thereby holding the transcatheter valve in a contracted position, or the catheter sheath may be withdrawn to a second position wherein the transcatheter valve is partially or completely exposed, thereby permitting the transcatheter valve to partially or completely expand.

In some examples, the transcatheter valve delivery assembly further includes a rotatable coupler that can be used to either tighten and secure or release a proximal end of the catheter sheath, to allow pushing or pulling of the catheter sheath to cover or uncover the sleeve and the valve coupled to the sleeve.

In some examples, the transcatheter valve delivery assembly further includes a release wire or release line that passes through the gimbal handle assembly and through the multi-lumen catheter, wherein a distal end of the release wire or release line passes through an aperture in the sleeve to the exterior of the sleeve and wraps around a circumference of the exterior of the sleeve.

In some examples, the multi-lumen catheter comprises a slotted ring affixed externally around the sleeve, located proximal to the plurality of apertures adjacent the distal end of the sleeve, wherein distal ends of each of the plurality of draw lines either loop around the release wire or release line or are removably attached to the release wire or release line by a single end of each draw lines, contacting the release wire or release line within a slot between two ring elements of the slotted ring, wherein pulling and withdrawal of the release wire or release line from its proximal end decouples the draw lines from the release wire or release line.

In some examples, the slotted ring is manufactured as an integral part of the sleeve.

In some examples, a distal portion of the release wire or release line is shielded in gaps between the ring elements and the sleeve and wherein the distal end of the release wire or release line passes back through an aperture in the sleeve and into a lumen in the multi-lumen catheter.

In some examples, distal ends of each of the draw lines are removably attached to the release wire or release line via a gap formed between filaments of each of the draw lines and secured with knots or by a single ended stringing configuration.

In some examples, the transcatheter valve delivery assembly further includes an imaging catheter that comprises an imaging probe at a distal end, wherein the imaging catheter is configured to pass through the gimbal handle assembly, the catheter and the valve, wherein the imaging catheter is configured to slide and move through the catheter and within the valve.

In some examples, the valve is a heart valve.

Some embodiments relate to a method of delivering a transcatheter valve to in a subject including:

obtaining the transcatheter valve delivery assembly according to claim 7, guiding the transcatheter valve to a position of implantation in a subject, releasing the transcatheter valve from the transcatheter valve assembly by pulling a proximal end of a release wire or release line so that the release wire or release line disengages from the plurality of draw lines; and removing the multi-lumen catheter and the sleeve attached to a distal end of the multi-lumen catheter from the subject.

In some examples, the is valve delivered and positioned in a native valve annulus.

In some examples, the guiding comprises tilting or laterally moving the transcatheter valve with respect to the longitudinal axis of the sleeve to achieve an optimal placement of the transcatheter valve.

In some examples, the gimbal handle is used to change a tilt angle of the attached valve and its enclosing frame with respect to the longitudinal axis of the sleeve by up to 60°.

In some examples, the gimbal handle spool is rotated in a direction to retract the plurality of draw lines and cause the valve frame to collapse from an expanded state, or wherein the gimbal handle spool is rotated in an opposite direction to release the plurality of draw lines and allow the valve frame to expand from a collapsed state to an expanded state.

In some examples, the transcatheter valve delivery assembly further includes an imaging device that passes through the gimbal handle, the catheter and the valve frame and valve, wherein the method comprises visualizing the position of implantation and surroundings in the subject while guiding the transcatheter valve into position.

BRIEF DESCRIPTION OF THE DRAWINGS

FIG. 3A. An example valve delivery system comprising a gimbal handle connected to a multi-lumen valve delivery catheter with a sleeve and an imaging system, wherein an expandable valve (in the expanded state) is coupled to the sleeve.

FIG. 9A illustrates an example of a sleeve connected to a multi-lumen catheter and coupled to a valve frame, wherein the draw lines, a release line or release wire and a valve frame are coupled based on stringing configurations described in U.S. Application publication No. 2018/0207010 A1 or U.S. Application publication No. 2016/0331566. In these configurations the distal end of each draw line, which is coupled to the release line/wire, is either single ended or secured by few knots.

DETAILED DESCRIPTION

Figure 1:
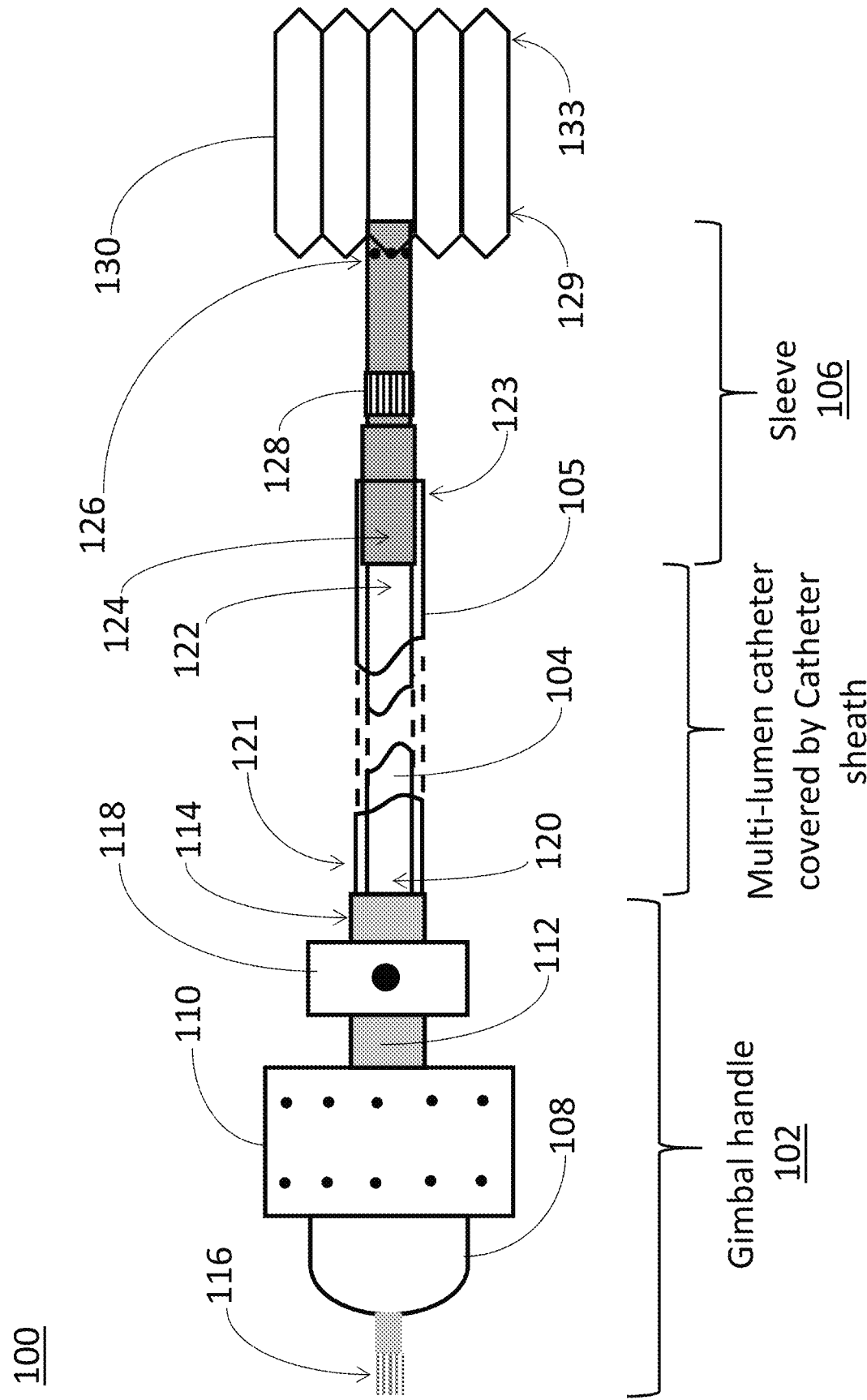
FIG. 1. Illustrates a two-dimensional side-view of the valve delivery system and an expandable valve (in the expanded state) according to an embodiment of the disclosed invention, for delivering, deploying and implanting a transcatheter valve into a patient.

The present invention relates to a medical device delivery system and, more particularly, a delivery system for delivery, deployment, implantation and repositioning of a transcatheter valve. The disclosed transcatheter valve delivery system, that provides improved control over implantation and, if necessary, repositioning of the valve, incorporates a gimbal handle connected to a valve delivery catheter, to which is releasably attached a valve stent frame via a sleeve, wherein the valve stent frame is expandable from a collapsed state to an expanded state.

The following description of certain embodiments presents various descriptions of specific embodiments. Although certain preferred embodiments and examples are disclosed below, inventive subject matter extends beyond the specifically disclosed embodiments to other alternative embodiments and/or uses and to modifications and equivalents thereof. As such, it will be apparent to one skilled in the art that the present invention may be practiced without necessarily being limited to these specific details. The innovations described herein can be embodied in a multitude of different ways, for example, as defined and covered by the claims. In this description, reference is made to the drawings, where like reference numerals indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings. In this description, references to "an embodiment," "one embodiment," or the like, mean that the particular feature, function, structure or characteristic being described is included in at least one embodiment of the technique introduced herein. Occurrences of such phrases in this specification do not necessarily all refer to the same embodiment. On the other hand, the embodiments referred to are also not necessarily mutually exclusive.

It should be noted that the gimbal handle assembly described herein can be used with a variety of medical device delivery systems. For example, FIG. 1 is provided as a non-limiting example of such a delivery system adapted to deliver a transcatheter valve; although it should be understood that the invention is not intended to be limited thereto.

FIG. 1 illustrates a 2D side-view of the valve delivery system 100 according to an embodiment of the disclosed invention, for delivering, deploying and implanting a transcatheter valve in a patient. Advantageously, this example incorporates a gimbal handle assembly 102 that facilitates precise deployment of the valve by providing additional degrees of freedom for controlling the orientation and position of the valve during an implantation procedure, not provided by previous designs and configurations. Due to its modular design, the gimbal handle assembly 102 can be also used in other medical device delivery systems to benefit from the provided additional degrees of freedom useful for controlling a stent frame. For example, the delivery system is not limited to the delivery of a valve device but could be used for precision delivery of therapy to a localized region through the use of a catheter. Such examples of delivery could include, but are not limited to, delivery of drugs or other therapeutic agents, delivery of RF irradiation, or delivery of another device other than an implantable valve.

The delivery system 100 comprises a gimbal handle 102, a multi-lumen catheter 104 inserted in a catheter sheath 105, and a sleeve 106. The gimbal handle 102 may include an outer gimbal 108, an inner gimbal (not shown), a spool 110, an elongate member 112 and a slide lock 118. The spool is rotatably coupled to the outer gimbal 108, such that it can freely rotate around the outer gimbal 108 (where the axis of rotation is the axes of symmetry for both spool 110 and outer gimbal 108). The outer gimbal 108 is rotatably coupled to the elongate member 112 such that the outer gimbal 108, and the spool 110 coupled to it, can be tilted in an arbitrary direction with respect to the longitudinal axis (e.g., axis of symmetry) of the elongate member 112. The elongate member 112 has a proximal end 116 that may be slotted and distal end 114 that is connected to the multi-lumen catheter 104. The multi-lumen catheter 104, that has a proximal end 120 and a distal end 122, can be a catheter tube with plurality of channels extended from its proximal end 120 to its distal end 122. The proximal end 120 of the multi-lumen catheter 104 is connected to the distal end 114 of the elongated member 112 of the gimbal handle 102 (e.g., using an adapter). The distal end 122 of the multi-lumen catheter 104 is connected to the sleeve 106. The sleeve 106 has a proximal end 124, connected to the distal end 122 of the catheter 104, and a distal end 126. The sleeve 106 may have a plurality of apertures. The sleeve 106 may also include a slotted ring element 128 surrounding the sleeve and affixed at position along the sleeve (e.g., proximal to its middle section).

In some embodiments, the length of the elongate member 112 of the gimbal handle can be between 3 inches and 18 inches, the length of the multi-lumen catheter 104 can be between 8 inches and 54 inches, and the length of sleeve 106 can be between 0.1 inches and 10 inches.

The delivery system 100 controls a valve frame 130 that can be removably coupled to the sleeve 106 via a plurality of draw lines (not shown). These draw lines mechanically couple the stent frame 130 of a valve to the gimbal handle 102 via all or a subset of the channels of the multi-lumen catheter 104. In some embodiments, each draw line passes through the at least one aperture on the valve frame 130, passes through at least one aperture on the sleeve 106, passes through one of the channels of the catheter 104, passes through the elongated member 112 of the gimbal handle 102, exits the elongated member 112 through one of the slots of its proximal end 116 and is secured to the spool 110. As such, in some examples, the proximal end of each draw line may be connected to the spool and its distal end may be coupled to the stent frame 130 of the valve and may be secured to the sleeve. In some embodiments, the distal end of each draw line may be removably secured to the distal end of a release line positioned underneath the slotted ring element 128 (see US 2018/0207010A1).

In some embodiments, rotating the spool 110 around the outer gimbal 108 pulls or releases the draw lines and therefore controls the tension on the struts in the stent valve frame 130 (that are coupled to the draw lines). By controlling the tension on the stent structure 130, the spool 110 can be used to control the state of expansion and contraction of the valve frame. Rotating the spool 110 around the outer gimbal 108 may pull or release all the draw lines equally enabling the control of the at least the proximal end 129 of the valve 130 valve frame from a collapsed state to an expanded state and vice versa. In some embodiment, the draw lines only control the proximal end 129 of the valve frame. In these embodiments, the degree of contraction, induced by pulling the draw lines, can be lower in the distal end 131 of the valve frame 130 compared to that of the proximal end 129 of the valve frame.

In some embodiments, at any given angular position of the spool 110 relative to the outer gimbal 108, the outer gimbal 108 and the spool 110 coupled to it, can be tilted with respect to the longitudinal axis of the elongate member 112. Tilting the spool with respect to the elongate member 112, selectively pull a subset of the plurality of draw lines while releasing the remaining of the draw lines (resulting in differential tension between the struts of the stent frame). As such, tiling the outer gimbal 108 and the spool 110 may be used to control the lateral position and orientation of the valve frame 130, with respect to the longitudinal axis of the sleeve 106. Advantageously, in these embodiments, during the manipulation, the valve frame can in a fully expanded state or partially contracted state. In other words, if the valve frame is not fully contracted (not touching the sleeve), it can be laterally displaced or tilted with respect to the sleeve. However, the maximum displacement or tilt angle may depend on the state of the frame. More detail about internal structure of the gimbal handle that allows the aforementioned motions and controls is described below.

During delivery, the distal end 123 of the catheter sheath 105 extends over the sleeve 106 and keeps both the proximal end 129 and the distal end 133 of the valve frame 130 fully contracted around the distal end of sleeve 106. Near the implantation region, the distal end 123 of the catheter sheath 105 is pulled back (by pulling its proximal end 121), such that the valve frame 130 is uncovered, thereby permitting controlled expansion or controlled retraction of valve frame 130. In some embodiments, once the catheter sheath 105 is pulled back, the state of the valve frame is controlled by the gimbal handle 102 through the draw lines. In some such embodiments, when the valve frame is uncovered, distal end 133 of the valve frame 130 expands and detaches from the sleeve while its proximal end 129 remains contracted by tension in the draw lines and may be in contact with the sleeve.

In some examples, the delivery system 100 may include a release wire or release line with a distal end coupled to the distal end of draw lines near the slotted ring 128. The release line may pass through sleeve 106, catheter 102, and elongated member 112, such that its proximal end comes out of the proximal end 116 of the elongated member 112. The release wire may be used to decouple the valve frame to the sleeve.

Figure 2:
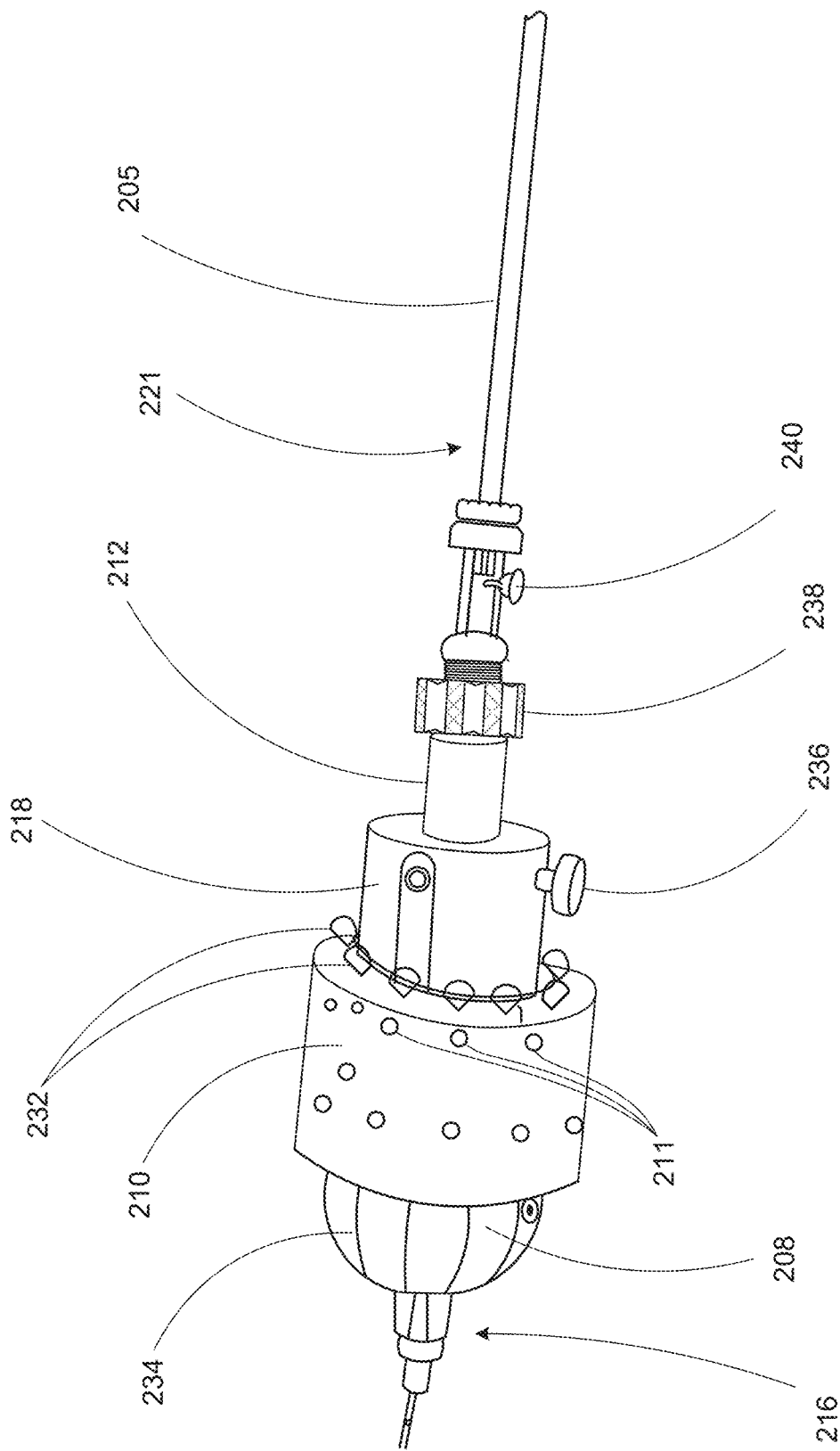
FIG. 2. Photograph of a gimbal handle and a proximal section of a valve delivery catheter.

FIG. 2 is a photograph of a gimbal handle assembly and a proximal section of catheter 204 of disclosed delivery system 100. The gimbal handle assembly comprises an outer gimbal 208, an inner gimbal (not visible), a spool 210, a plurality of hooks 232 circumferentially positioned on the edge of the spool 210, a slide lock 218, an elongate member 212, a set screw 236 that may be used to lock the slide lock 218 to the elongate member 212, a rotatable coupler 238 that can be used to tighten/secure or release proximal end 221 of catheter sheath 205, to allow pushing or pulling of sheath 205 (to cover or uncover the sleeve and the valve coupled to it), an adapter 240 that connects the rotatable coupler 238 to the catheter sheath 205 and catheter 204 within. The gimbal handle further comprises, a plurality of draw lines 234 connected to the spool 210 via the plurality of adjustable hooks 232 (e.g., metallic circular hooks) circumferentially mounted around one edge of spool 210. Each hook 232 is mounted using a set screw 211 on the spool 210. The draw lines 234 pass through an internal cavity of spool 210, a plurality of channels provided on the outer gimbal 208, going over the outer gimbal 208 and enter the elongate member 212 through its slotted proximal end 216.

FIG. 3A is schematic diagram illustrating an embodiment of a transcatheter valve delivery system comprising a gimbal handle assembly 302, a multi-lumen catheter (not shown) covered by a catheter sheath 305, an image sensor 348, an imaging cable 344 and a display system 342. Also shown are spool 310, elongated member 312 and slide lock 340. The imaging sensor can be an ultrasonic sensor (e.g., IVUS), an OCT sensor, a CCD camera, a fiber-optic imaging head and the like. The display system can be a custom-made display system, a notebook, a tablet, a smart phone, a desk top computer, and the like. In some examples, an adapter 346 may be attached to the distal end of the elongate member to provide access to the catheter tube. In the example illustrated in FIG. 3A, the catheter sheath 305 is not covering the valve 330 that is fully expanded.

Figure 3B:
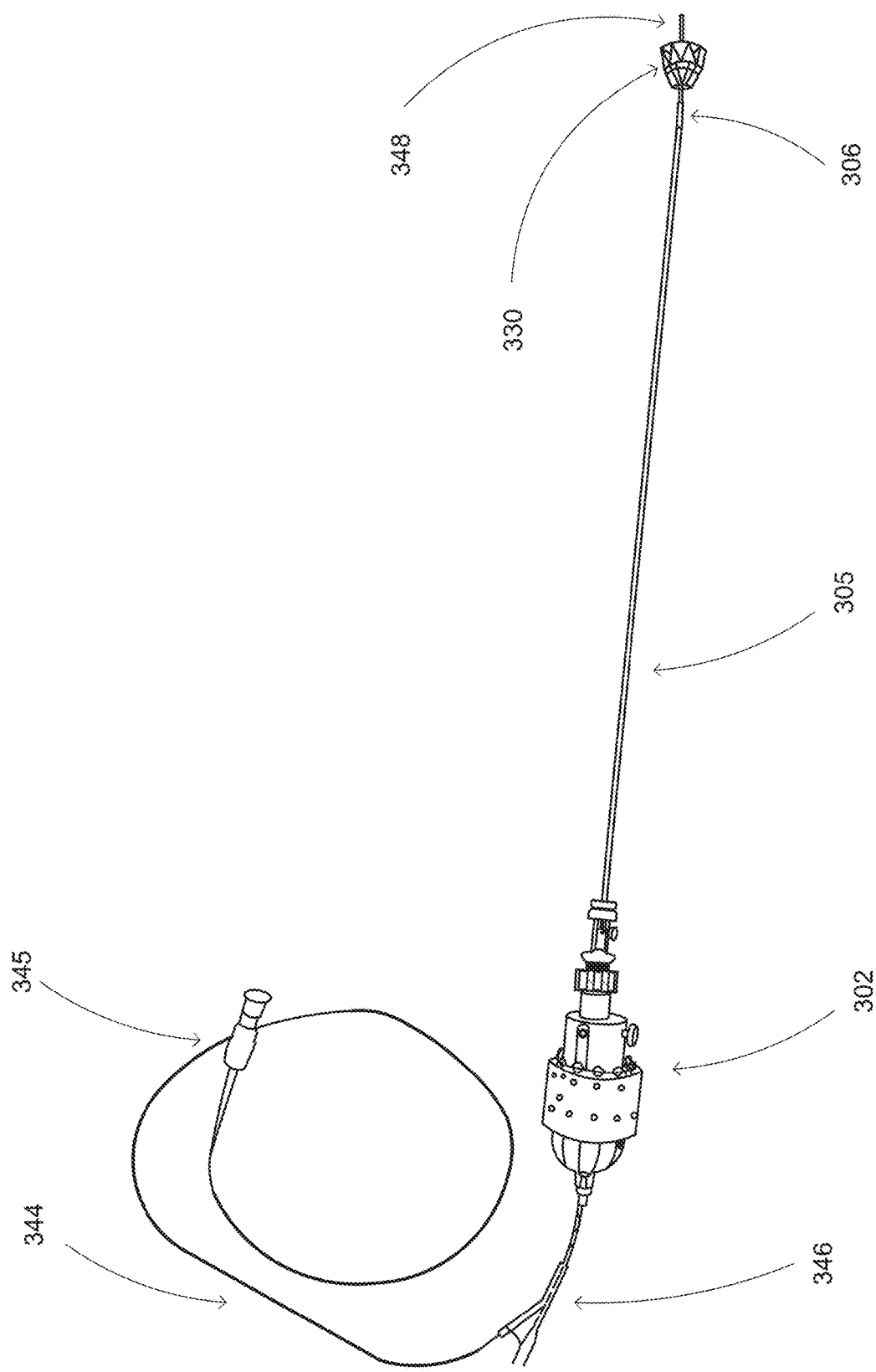
FIG. 3B. Photograph of a delivery system coupled to a transcatheter valve.

FIG. 3B is a photograph of an embodiment that is an embodiment of the disclosed delivery system 100 linked to a transcatheter valve 330. In addition to the gimbal handle 302, multi-lumen catheter (not observable), catheter sheath 305 covering the catheter and sleeve 306. This example is also equipped with an IVUS catheter comprising an ultrasonic imaging sensor 348 that passes through the sleeve 306 and is electrically connected to an electric connector 345

(e.g., BNC connector) via a cable 344 (e.g., a BNC cable) that passes through the sleeve, through one of the channels of the multi-lumen catheter (e.g., central channel), through the elongate member and exits through the proximal end of the elongated member. A Y-shaped adapter 346 is attached to the distal end the elongate member such that in addition to the electrical cable 344, another wire or cable (e.g., a guide wire) can be inserted through the elongate member.

Gimbal Handle

Figure 4A:
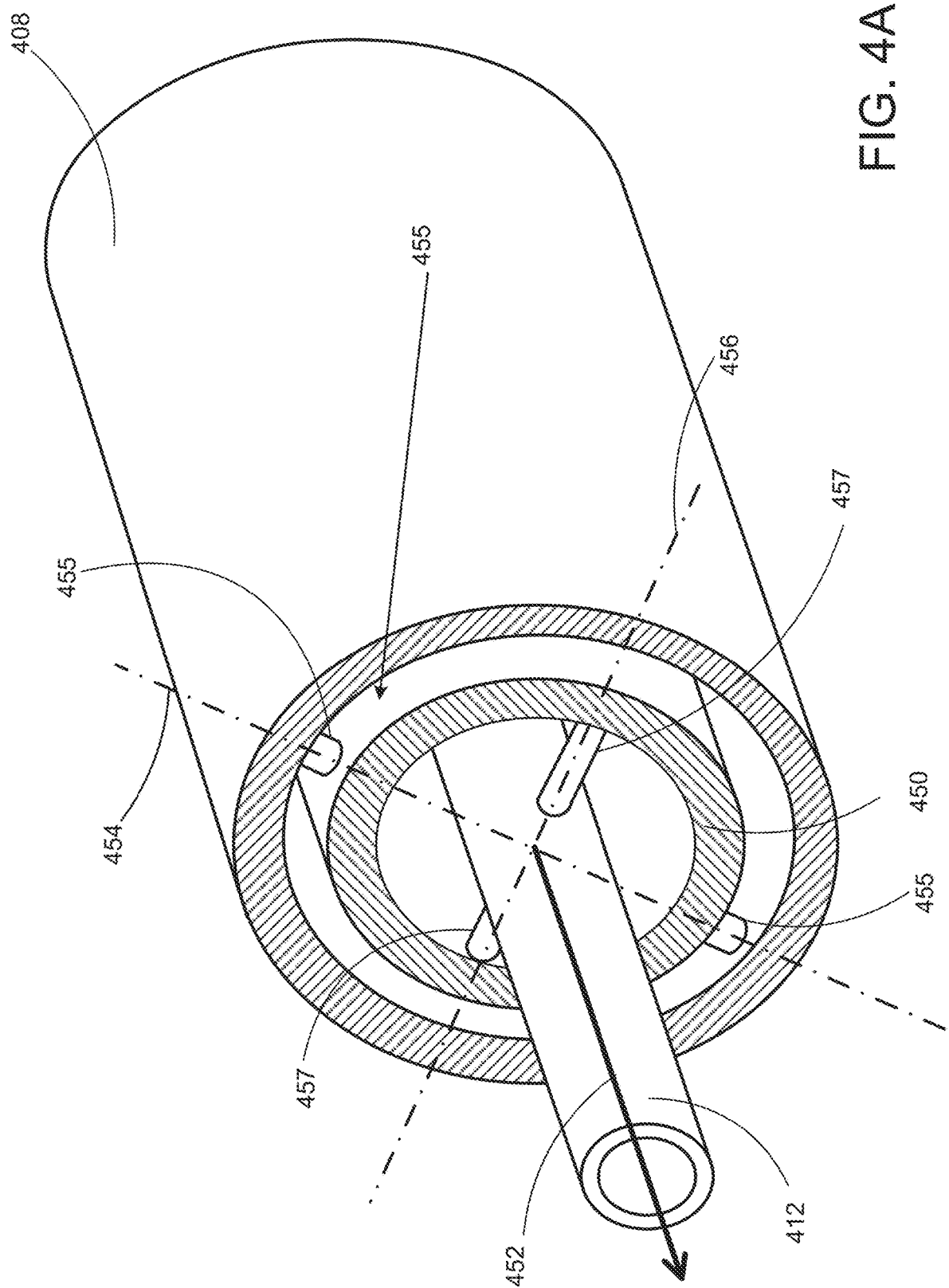
FIG. 4. (A) Diagram illustrating internal joints of the gimbal handle assembly. (B) The coordinate system defining tilt angles associated with pitch and yaw of the outer gimbal with respect to the elongate member.
Figure 4B:
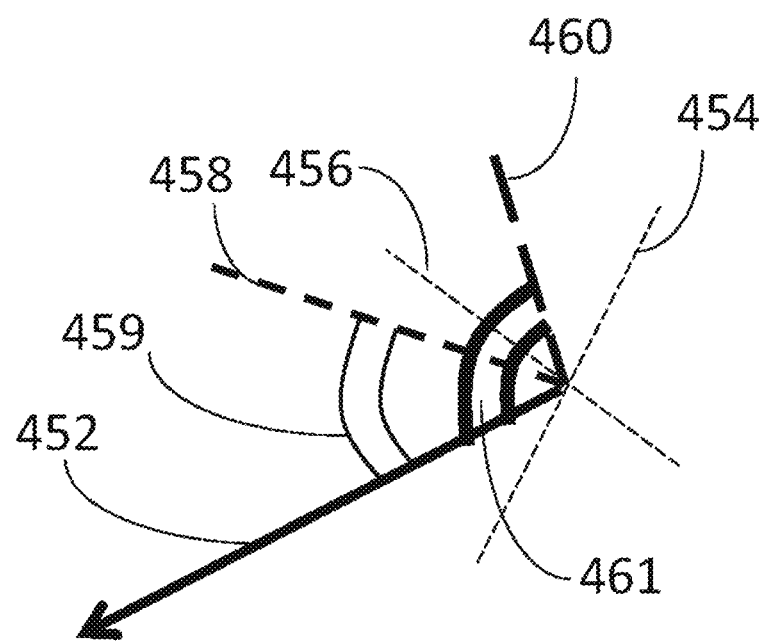

As described above, the gimbal handle 102 includes a set of two gimbals (inner gimbal and outer gimbal 108) and spool 110, which is coupled to and rotatable within and around outer gimbal 108. The pair of gimbals allow spool 110 to be tilted along an arbitrary direction with respect to the longitudinal axis of the elongate member 112 of the gimbal handle. FIG. 4, (A) is a simplified diagram that illustrates the internal joints of the gimbal handle assembly that provide two rotational degrees of freedom needed to tilt the spool 110 with respect to the elongate member 412. The outer gimbal 408 is coupled to the inner gimbal 450 by a first rotatable joint with a first pivot axis 454, that is orthogonal to the longitudinal axis 452 of the elongate member 412 and around which gimbal 408 can pivot. Such a joint can be created, for example, using a pair of rods 455. The inner gimbal 450 is coupled to the elongate member 412 by a second rotatable joint with a second pivot axis 456 that is orthogonal to both the first pivot axis 454 and the longitudinal axis 452 of the elongate member 412, around which the elongate member 412 and the inner gimbal 450 can pivot. Such a joint can be created, for example, using a second pair of rods 457. The combination of these two rotational degrees of freedom (i.e., around the first 454 and the second 456 pivot axes), allows tilting of the outer gimbal 408 (and the spool coupled to it) to a desired direction with respect to the longitudinal axis 452 of elongate member 412.

The rotational degrees of freedom of the gimbal assembly may be described based on pitch, yaw and roll. These terms are commonly used to describe an object's three-dimensional rotational movement through a space. In the context of the gimbal assembly of the disclosed delivery system, these terms may be used to describe the movement of the outer gimbal 408 and the spool coupled to it, relative to a fixed longitudinal axis 452 of the elongated member 412. Yaw may refer to the motion of the spool and the outer gimbal 408 resulting from only pivoting the outer gimbal 408 around the first pivot axis 454. Pitch may refer to the motion of the spool and the outer gimbal 408 resulting from only pivoting the inner gimbal 450 around the second pivot axis 456. Roll relates to circular movement of the spool or outer gimbal around their own axis of symmetry (that may be parallel with or tilted relative to the longitudinal axis 452 of the elongate member 412). Note that the spool is symmetrically mounted on the outer gimbal 408 so the spool and the outer gimbal share a single same axis of symmetry. For a fixed position of the elongate member 412, only the spool can be rolled (around the outer gimbal).

With reference to FIG. 4, (B), the tilt angles associated the pitch and yaw, can be defined based on the on the coordinate system defined by the first 454 and second 456 pivot axes, and the longitudinal axis 452 of the elongated member 412. The pitch angle 459 is the angle between the axis of symmetry 458 of the outer gimbal and the longitudinal axis 452 of the elongate member 412, if only the outer gimbal is pivoted around the first pivot axis 454. The yaw angle 461 is the angle between the axis of symmetry 460 of the outer gimbal and the longitudinal axis 452 of the elongate member 412, if only the inner gimbal is pivoted around the second pivot axis 456.

The pitch and yaw angle of the spool/outer gimbal each may be changed by up to ±60°, including the following exemplary values there-between: −60°, −55°, −50°, −45°, −40°, −35°, −30°, −25°, −20°, —15°, −10°, −5°, 0°, 5°, 10°, 15°, 20°, 25°, 30°, 35°, 40°, 45°, 50°, 55°, 60°.

Figure 5A:
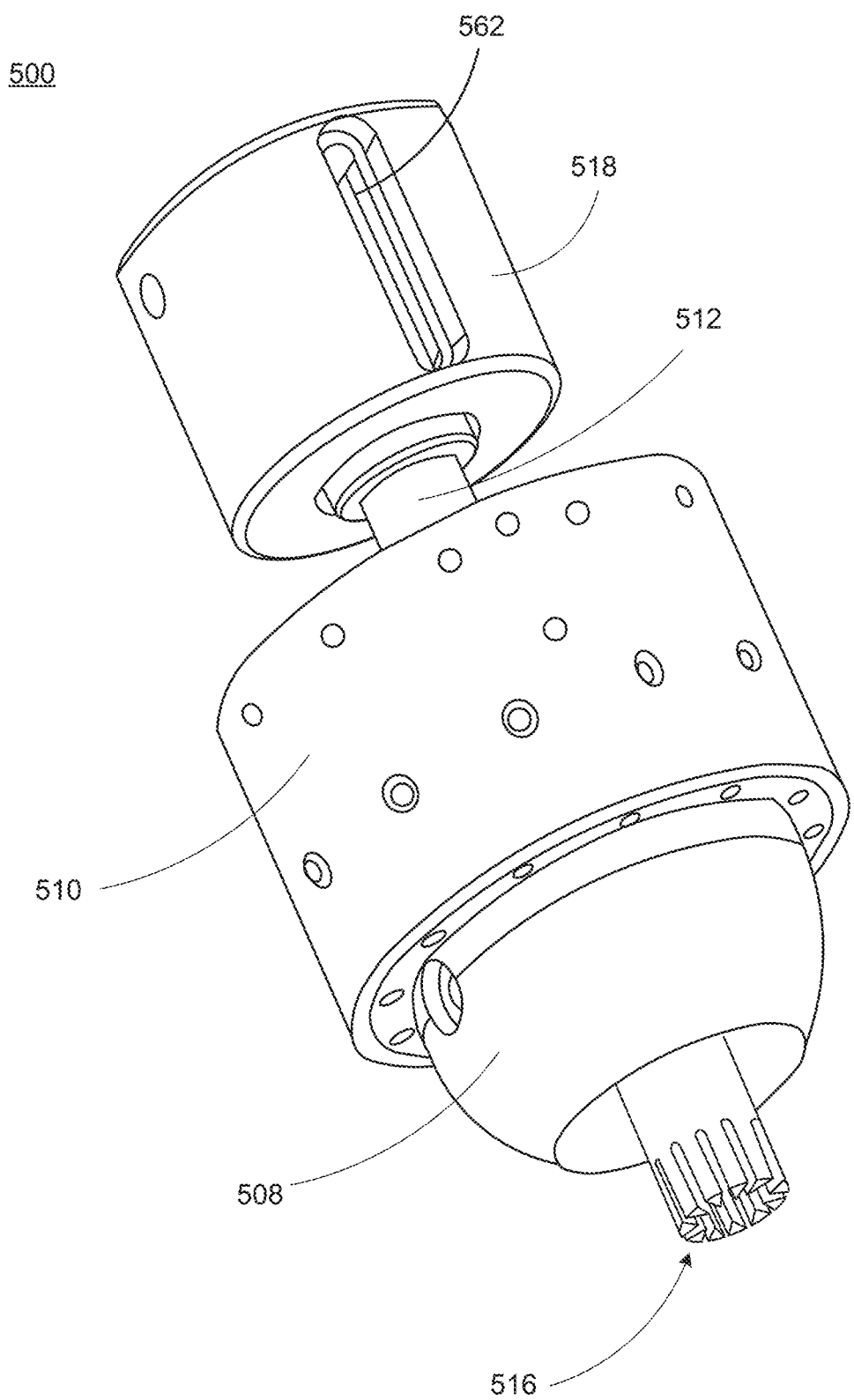
FIG. 5. (A) perspective view of an example embodiment of the gimbal handle assembly comprising an elongate member, a slide lock, a spool, an outer gimbal and an inner gimbal (not shown). (B) Cross-sectional view of the gimbal assembly illustrating the arrangement and coupling between the constituents of gimbal assembly. (C) Perspective views of the spool (C1), outer gimbal (C2) and inner gimbal (C3) of the gimbal assembly shown in FIG. 5A.
Figures 5B, 5C:
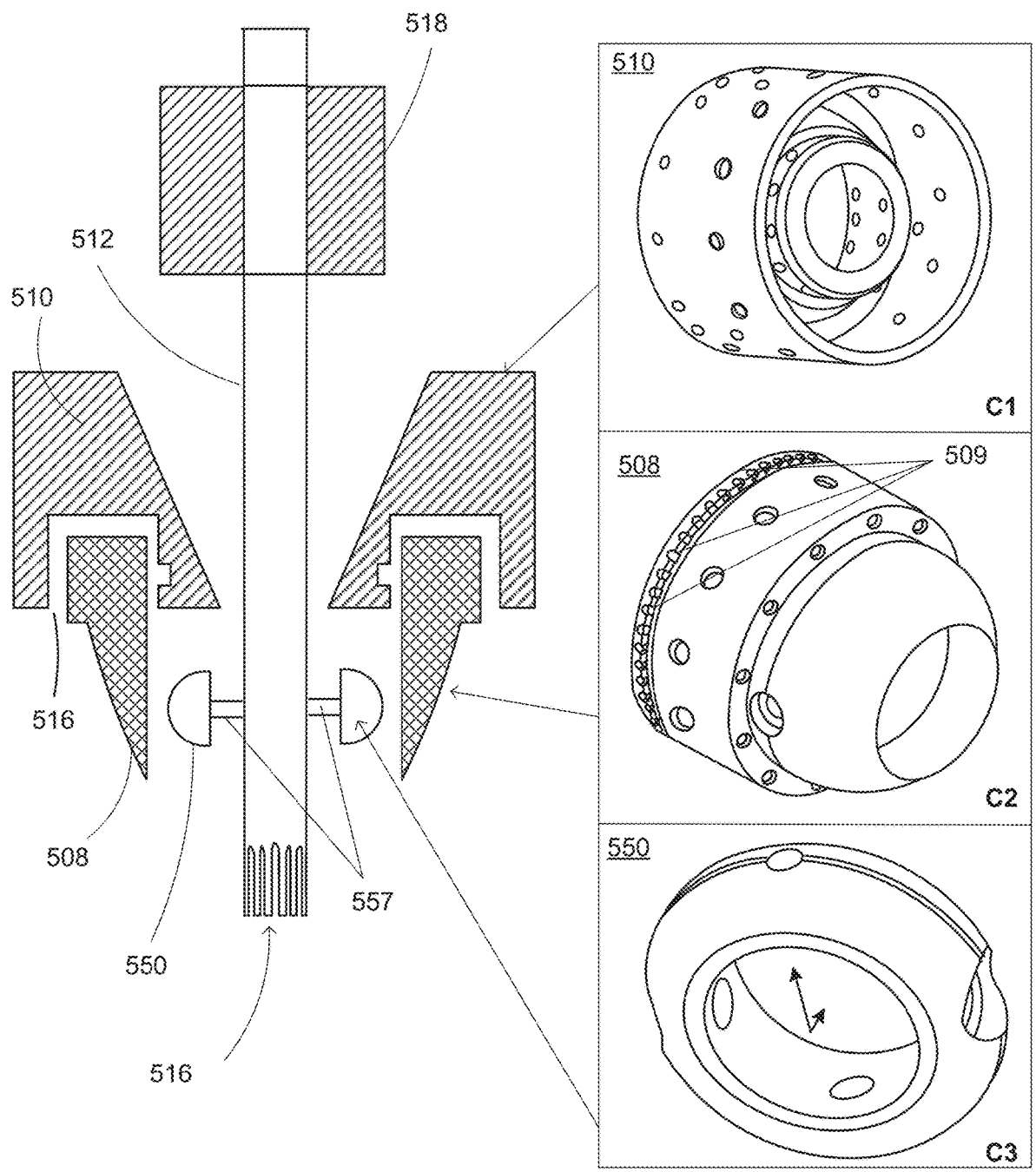

FIG. 5, (A) is a perspective view of an example embodiment of the gimbal handle assembly 500 comprising an elongate member 512, a slide lock 518, a spool 510, an outer gimbal 508 and an inner gimbal (not shown) and a proximal end (516) of elongate member 512. FIG. 5, (B) shows a cross-sectional view of the gimbal assembly 500 illustrating the arrangement and coupling between the constituents of gimbal assembly 500. The spool 510 is a cylinder with a conical hole and a circular slot 561 formed on one of its bases in which the outer gimbal 508 can be inserted into and freely rotate around it. The outer gimbal 508 is a hollow cylinder with wall thickness that changes in a step wise manner near the middle of it height. The thinner section of the outer gimbal 508 is shaped like a dome. In some embodiments, the thicker section of the outer gimbal 508 may have a plurality of slots 509 (e.g., equally spaced slots) formed at the edge of its base. These slots 509 can be used to control the rotation of the spool 510 around the outer gimbal 508, for example, stabilizing the angular position of the spool 510 in a step wise manner, wherein the minimum rotation angle (corresponding to rolling motion of the spool 510) resulted from rotating the spool 510 by one step is limited by the spacing between the slots 509. In some such embodiments, the minimum angle of rotation can be between 0° and 10°, including the following exemplary values there-between: 1°, 2°, 3°, 4°, 5°, 6°, 7°, 8°, and 9°. The outer gimbal 508 is coupled to the inner gimbal 520, that is shaped like a toroid, by a first rotatable joint (not shown), for example, comprising two rods aligned along a first pivot axis that is orthogonal to the elongate member 512. The inner gimbal 550 is coupled to elongate member 512 by a second rotatable joint, for example, another pair of rods 557 aligned along the second pivot axis that is orthogonal to both elongate member 512 and the first pivot axis. In this example, the slide lock 518 is shaped as a cylinder with hole in the center through which the elongate member 512 passes. The diameter of the hole and the elongated member may be selected such that slide lock 518 can smoothly slide along the elongate member 512 without being tilted relative to the longitudinal axis of the elongate member 512. An elongated hole 562, depicted in FIG. 5(A) is provided on the lateral area of slide lock parallel to its axis of symmetry. This hole 562 allows using a screw (not shown) to affix the slide lock 518 at any given position along the elongate member 512. If the slide lock 518 is affixed inside the conical hole of spool 510, it may lock both gimbals and the spool in a symmetrical position with respect to the elongate member 512, hereto referred to as the neutral position. When locked in the neutral position, none of the gimbals or the spool can pivot in any direction with respect to the longitudinal axis of the elongate member 512. FIG. 5, (C1-C3) show perspective views of spool 510, outer gimbal 508 and inner gimbal 550 of the gimbal assembly shown in FIG. 5, (A).

In some embodiments the spool can have a dimeter between 1 inch and 4 inches, with a conical hole that may have height between 0.2 inch and 3 inches, a large diameter between 0.8 inches and 3.8 inches, and a small diameter between 0.4 inches and 3.2 inches. The cylindrical section of the outer gimbal may have diameter between 0.4 inch and 3 inches, and its dome-shaped section may have a diameter between 0.36 inch and 2.96 inch. The inner gimbal may have a major diameter between 0.3 inch and 2 inches, and a cross-sectional minor diameter between 0.2 inch and 1 inch. The gimbals, the spool and the elongate member, may be formed from various metals, metal alloys (e.g., aluminum, brass, steel, and the like), a polymer (e.g., polystyrene or polyurethane) or plastic. In some embodiments, all the components of the gimbal assembly 500 may be formed from a single material. In some other embodiments, the components of the gimbal handle assembly 500 may be formed form one or more materials.

Figure 6A:
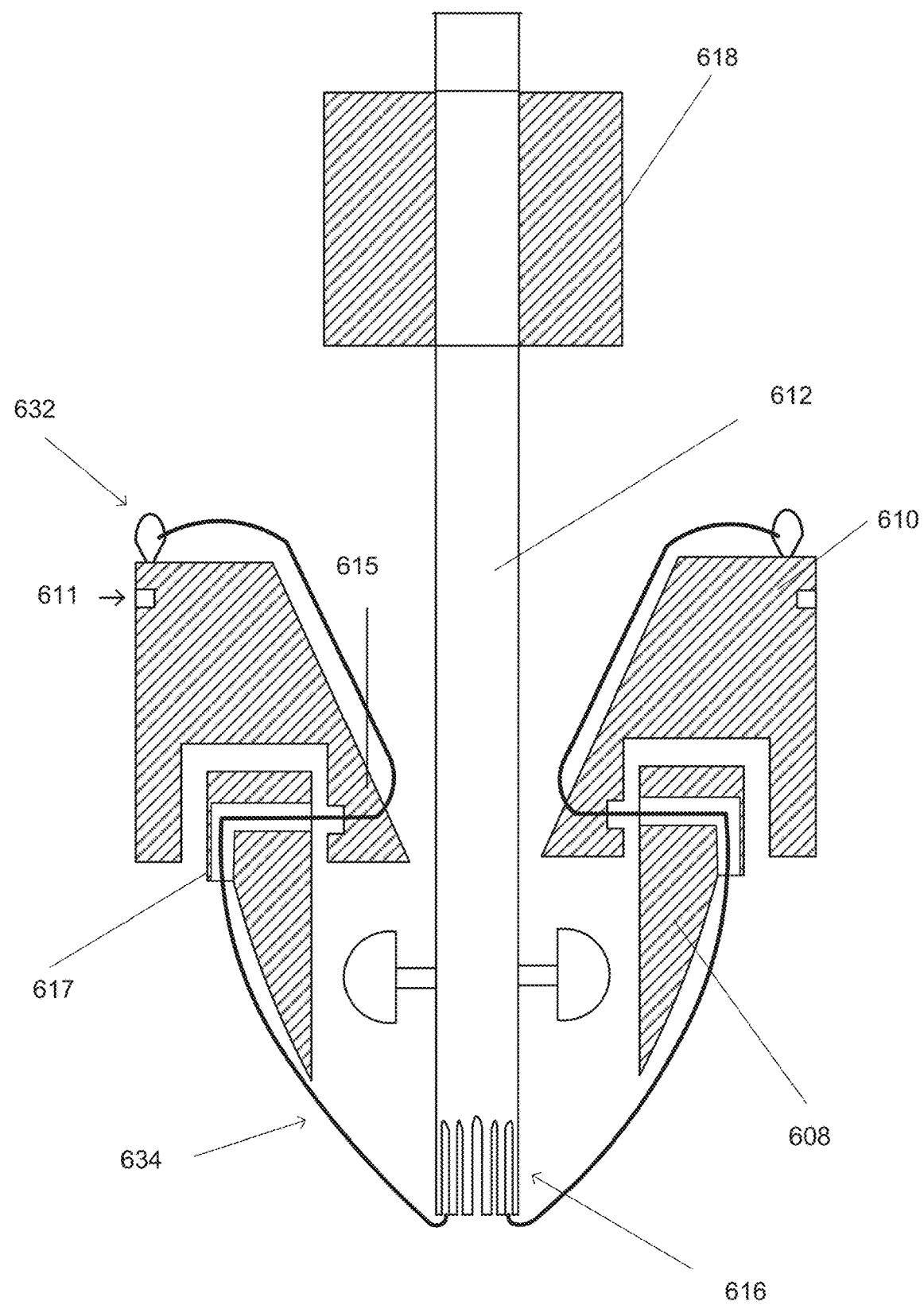
FIG. 6. (A) Cross-sectional view of the gimbal assembly illustrating the arrangement and coupling between the constituents of the gimbal assembly and draw lines. (B) A photograph of the gimbal handle assembly locked in the neutral position.

In some embodiments, a plurality of draw lines are connected to the spool in a circumferential configuration. As shown in FIG. 6, (A) (a cross-sectional view of an example embodiment), the proximal ends of the draw lines 634 are attached to plurality of hooks 632 circumferentially mounted on the edge of the spool 610 using a plurality of set screws 611. These set screws 611 can be used to tune the position/orientation of each hook 632. The draw lines 634 pass through the conical hole of the spool, through a plurality of apertures 615 in the spool 610, through a plurality of channels and/or apertures 617 in the outer gimbal 608 and enter the elongate member 612 through the plurality of slots provided on its proximal end 616. After passing through the elongate member 612, the multi-lumen catheter attached to it, and the sleeve attached to the catheter, the distal end of these draw lines 634 mechanically couple the spool 610 to the stent frame of a valve that may be delivered using the delivery system. Rotation of the spool 610 around the outer gimbal 608 (rolling movement) causes the draw lines to wrap around the spool 610. The clockwise or the counterclockwise rotation of the spool 610 may pull or release the proximal ends of all draw lines 634 symmetrically and by a same amount. Consequently, the tension and position of the distal ends of draw lines can be controlled by changing the rotational state of the spool 610. If the spool is locked in the neutral position (wherein pitch angle 459 and yaw angle 461 are both equal to zero, see FIG. 4(B) by the slide lock 618, its rotation pulls or releases all the draw lines of the plurality of draw lines symmetrically and by the same amount. If the spool is unlocked and it is tilted with respect to the elongate member (pitch and yaw movement), the draw lines will be pulled and/or released asymmetrically. The uneven distribution of tension among the draw lines, when the spool is in a tilted state, depends on the tilt angle and tilt direction of the spool (determined by the degree of pitch and yaw). As such, by controlling the role, pitch and yaw of the spool, a user may precisely control a differential tension among all the draw lines. Thus, the gimbal handle provides a means to tighten or loosen all draw strings simultaneously by equal amount by rotation of the spool and to selectively tighten and loosen draw strings by differential amounts by controlling the pitch and yaw, FIG. 6, (B) is a photograph of the example gimbal assembly shown in FIG. 6A when the spool is locked in the neutral position by the slide lock. In this example, a plurality of rings 632 are mounted circumferentially around one edge of the spool 610. These rings 632 may be used to secure the proximal end of the draw lines 634 to the spool 610. Upon rotation of spool 610, the draw lines 634 may be wrapped around the spool 610.

Figure 6B:
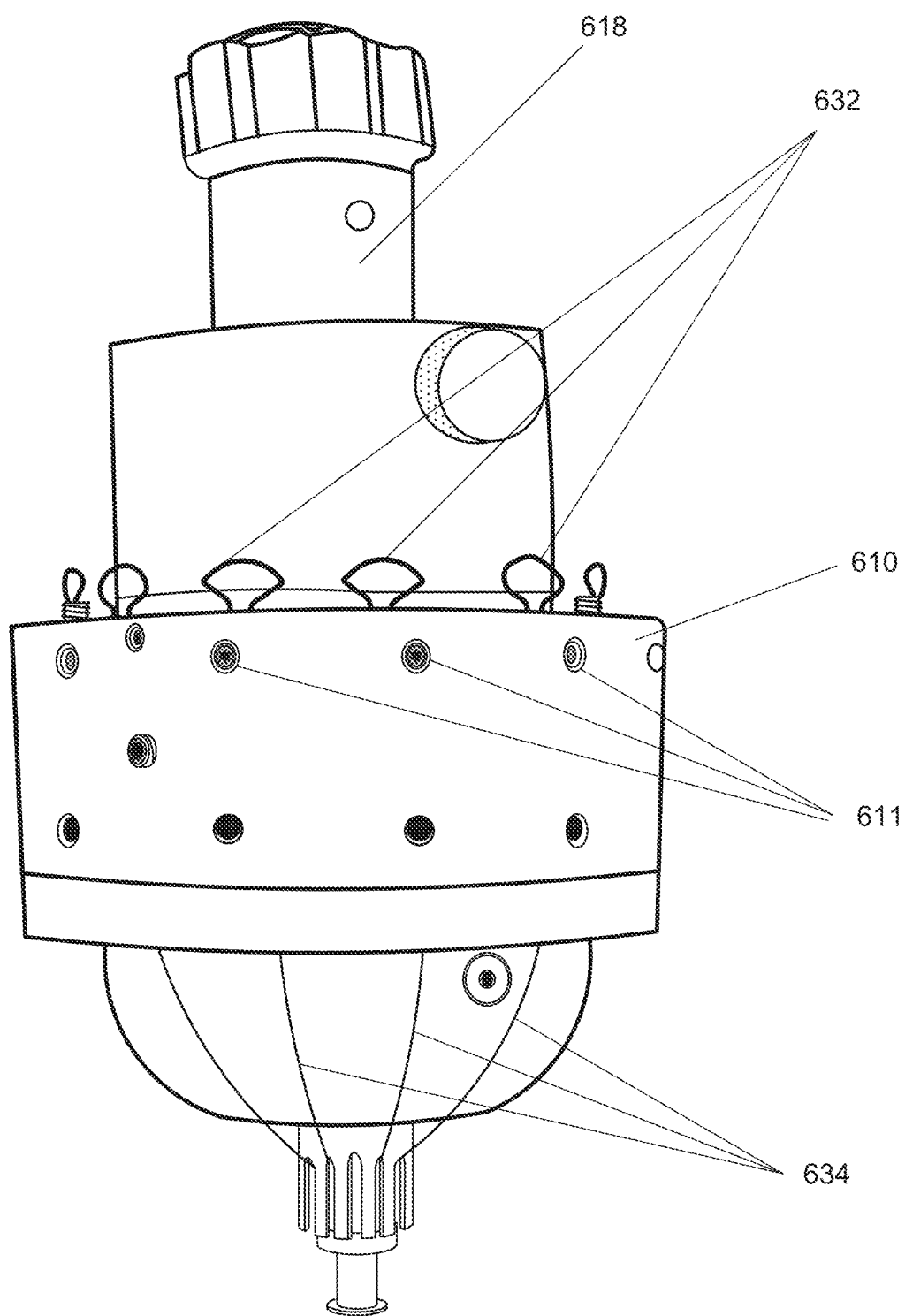
Figure 7A:
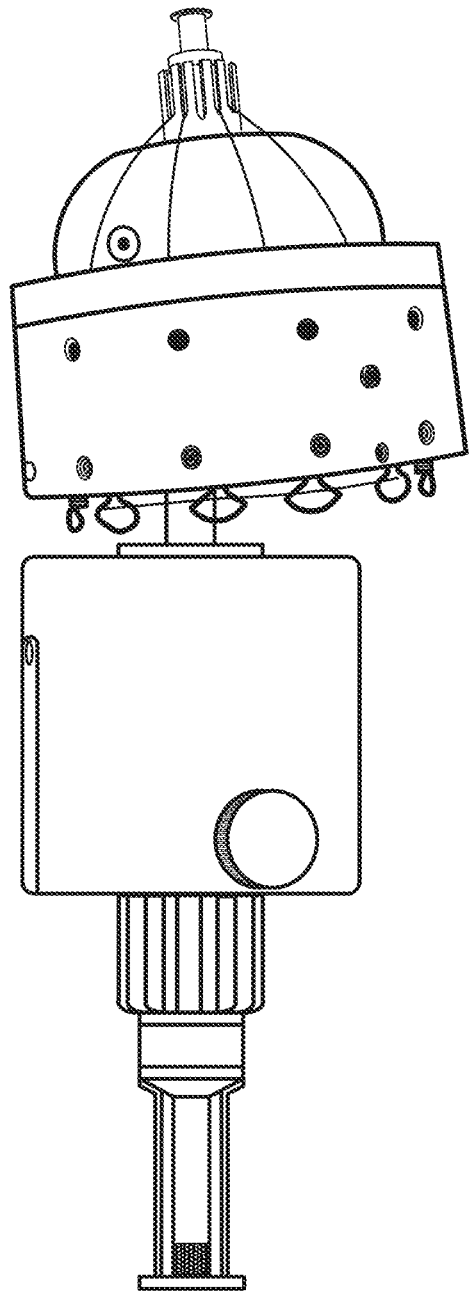
FIG. 7. (A)-(D) Photographs of the prototype shown in FIG. 6B as the spool is swiveled through various orientations with respect to the elongate member. The handle gimbals and spool are tilted, causing selective tightening and releasing of the draw lines corresponding to the position of the draw lines around the gimbal, which causes a corresponding change in the tilt of an attached expandable valve relative to the sleeve.
Figure 7B:
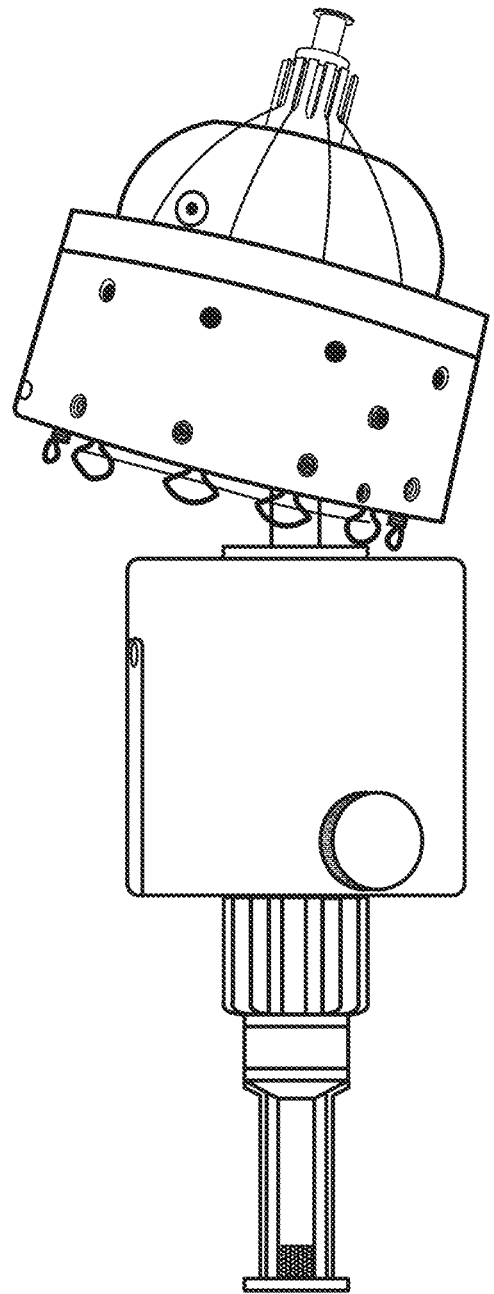
Figure 7C:
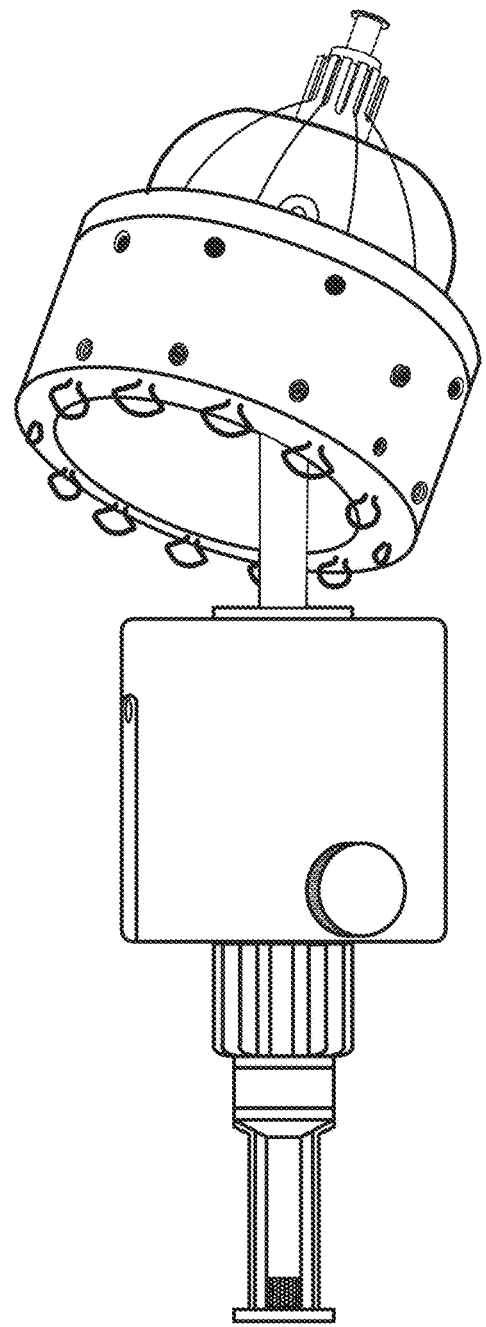
Figure 7D:
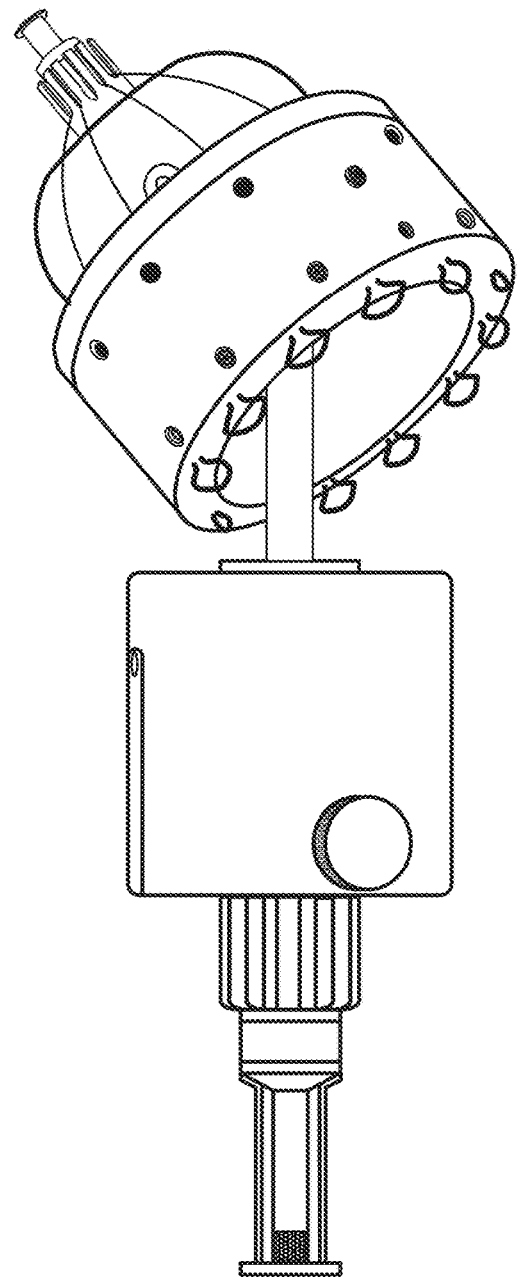

FIG. 7(A)-(D) show photographs of the example embodiment shown in FIG. 6B as the spool is swiveled through various orientations with respect to the elongate member (here the slide lock is pulled out of the spool to enable free rotation).

In addition to the draw lines, a release wire may also pass through the elongate member, exit from its proximal end 616 and be attached to the elongate member 612, such that the release wire or release line can be pulled proximally.

The Catheter and the Sleeve

In some embodiments, the gimbal handle assembly may be connected (e.g., using an adapter) to a multi-lumen catheter with a sleeve attached to the distal end of the multi lumen catheter. The sleeve can be a cylindrical shell and may have a plurality of apertures that allow the draw lines, which are connected to the gimbal handle assembly and passing though the multi-lumen catheter, to be linked to the stent frame of a valve.

Figure 8A:
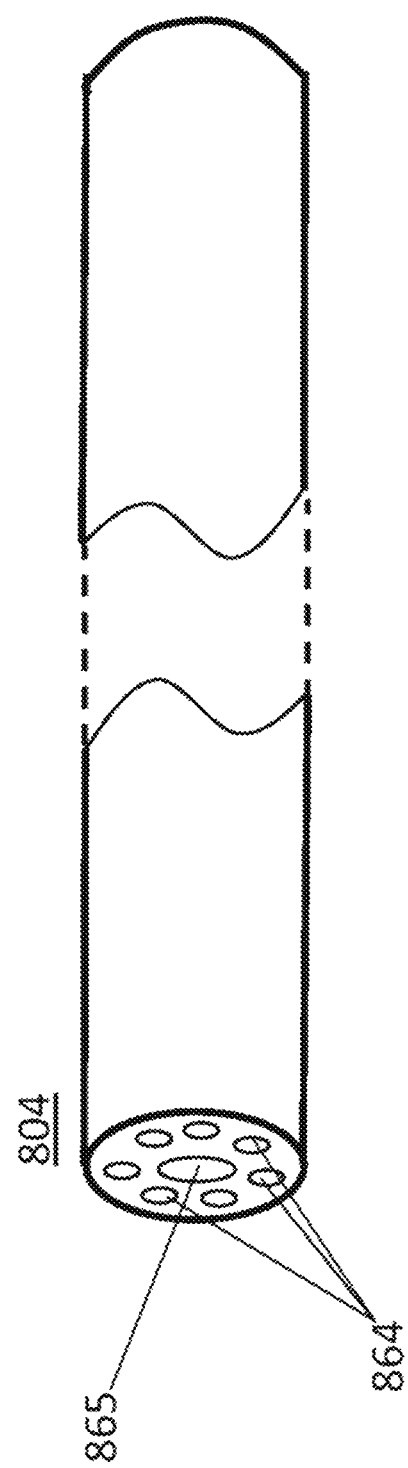
FIG. 8. (A) Illustrates a perspective view of an example of a multi-lumen catheter tube with a central hole and a plurality of peripheral holes. (B) Illustrates a perspective view of an example sleeve with a plurality of apertures near its distal end, a slotted ring and release wire/line aperture. (C) An example of a connection between a multi-lumen catheter and a sleeve.

FIG. 8, (A) is an illustration of an embodiment of the multi-lumen catheter 804. In this embodiment a plurality of channels (lumens) 864, that may have equal or different diameters, are arranged circumferentially close to the peripheral surface of the catheter, while a single channel 865 with a diameter larger than the peripheral channels 864 is provided at the center of the multi-lumen catheter 804. In some embodiments, the peripheral channels 864 may be used to pass a plurality of draw lines and at least one release wire, while the central channel 865 may be used to pass a guide wire, a conductive cable (e.g., a coaxial cable) and/or an imaging optical fiber (e.g., a multicore imaging optical fiber or an optical fiber bundle). The multi-lumen catheter 804, may be formed of plastic materials (e.g., nylon, polypropylene or polystyrene) and may have a diameter between 0.06 inch and 0.3 inch. The central hole may have a diameter between 0.03 inch and 0.2 inch, and the peripheral holes may have diameters between 0.006 inch and 0.04 inch. In some embodiments, the multi-lumen catheter may be a flexible catheter. In some other embodiments the catheter may be a rigid or semi-rigid catheter.

FIG. 8, (B) illustrates an embodiment of the sleeve 806, a cylindrical shell with a plurality of holes 866 circumferentially arranged adjacent to the distal end 826 of sleeve 806. Sleeve 806 can be formed from a metallic (e.g., aluminum), plastic or polymeric material and may have an inner diameter between 0.06 inch and 0.3 inch, and an outer diameter between 0.07 inch and 0.31 inch.

Slotted Restraining Ring

The sleeve 806 may include a slotted restraining ring that includes ring element 828 with a plurality of slots 870. Ring element 828 may have a diameter between 0.07 inch and 0.32 inch, a thickness between 0.005 inch and 0.06 inch. The total number of slots can be between 1 and 30, and each slot may have a width between 0.002 inch and 0.03 inch. The slots may extend a part of or the full length or of the ring element 828. Slotted restraining ring 828 may be made as an integral part of the sleeve or may be made separately and attached to the sleeve. On a portion of the slotted ring element 828, the internal diameter of the ring element is larger than the outside diameter of the sleeve body such that there is a gap between the slotted ring element and the sleeve.

Advantageously, the slotted restraining ring is externally affixed to the outside of sleeve 806, thereby permitting draw strings in communication with the valve to externally tether a valve frame to the slotted restraining ring on sleeve 806. Locating the attachment of the draw lines external to the sleeve, i.e., outside of the multi-lumen catheter 804 and sleeve 806, significantly increases the volume capacity within sleeve 806 and multi-lumen catheter 804.

Figure 8B:
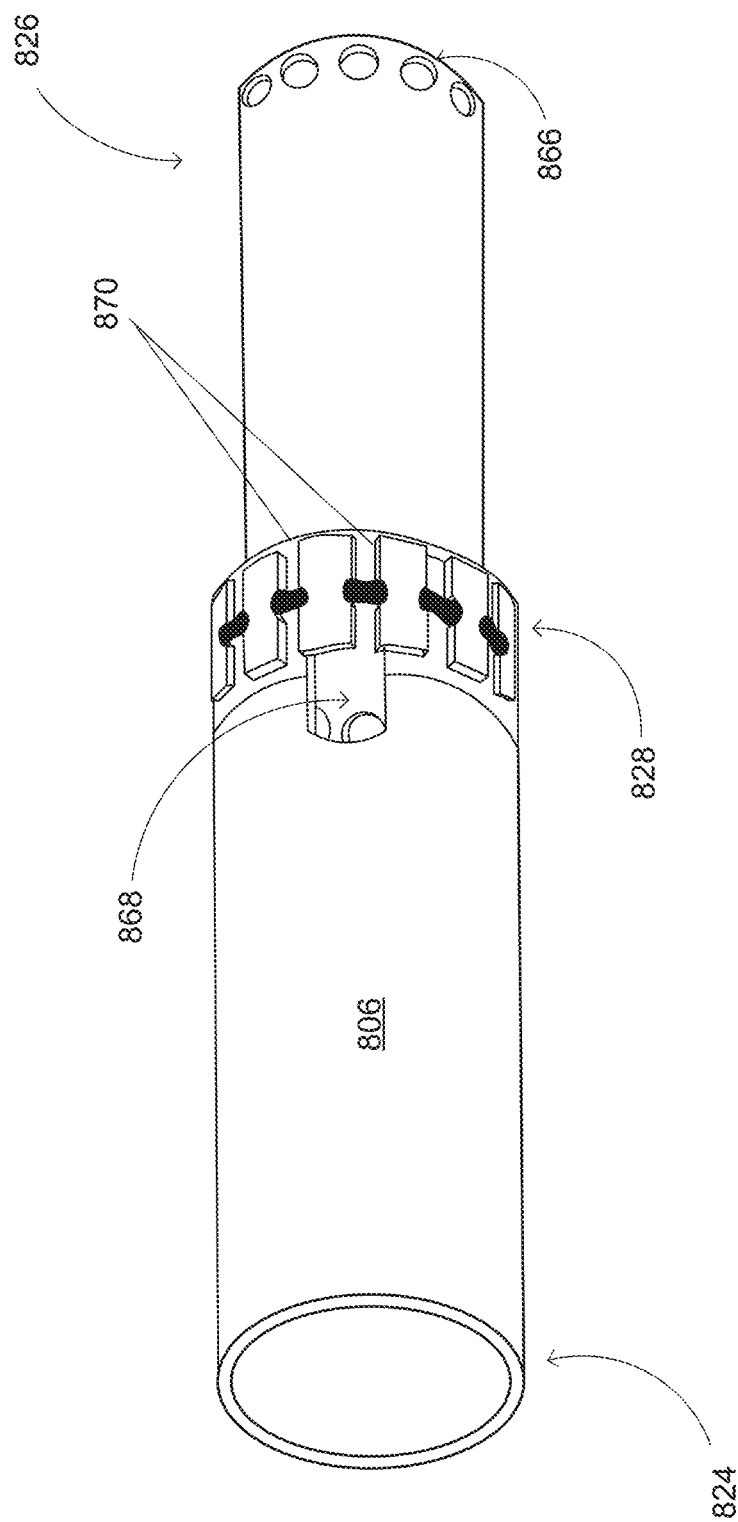
Figure 8C:
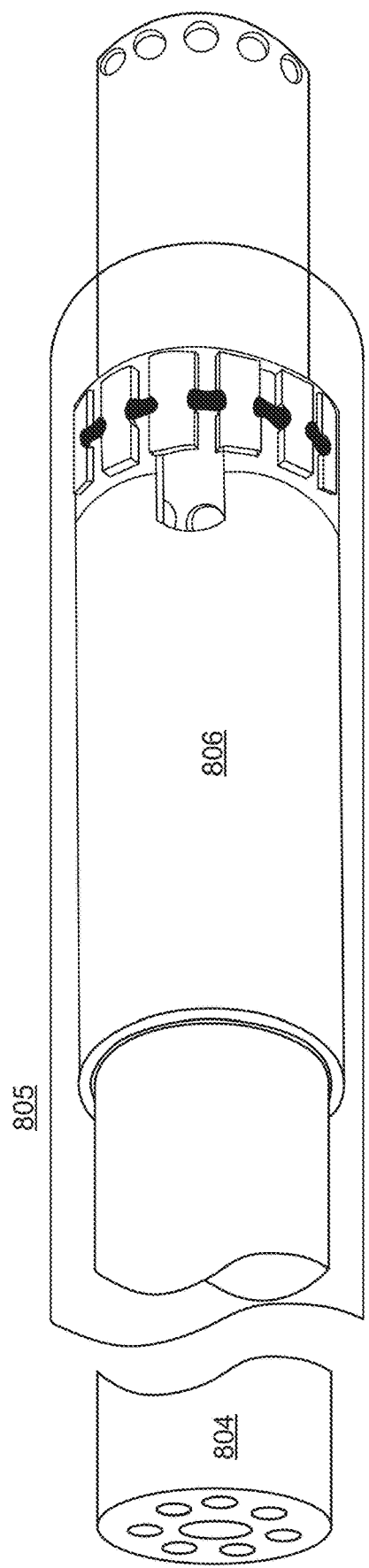

In the example shown in FIG. 8B, the outer diameter of the sleeve 806 changes in a stepwise manner near the middle of the sleeve such that, the diameter of the proximal end 824 of the sleeve is larger than the diameter of the distal end 826 of the sleeve 806. The ring element 828 is positioned/attached on the section with the smaller diameter close to the middle of the sleeve (where the diameter abruptly changes). In some embodiments (shown in FIG. 8C), the inner diameter of the proximal end 824 of the sleeve is larger than the outer diameter of the distal end 822 of the catheter such that the distal end 822 of the catheter 804 may be inserted into the proximal end of sleeve 806. In some other embodiments, a catheter sheath 805 may cover the multi-lumen catheter 804 from its proximal end to its distal end (that is attached to the sleeve 806). In some such embodiments, the catheter sheath 805 can be moved back and forth over the multi-lumen catheter 804 along its length. In these embodiments, the catheter sheath 805 can be moved all the way to the distal end 826 of the sleeve 806 and completely cover sleeve 806. When a stented valve is coupled to sleeve 806, sheath 805 may cover sleeve 806 and the expandable valve coupled to it, to keep the valve frame in the collapsed state (in contact with the sleeve 806) during the delivery period. At or near the valve implantation location (e.g., towards the left ventricle (LV) or the ascending aorta), the sheath can be gradually pulled back to uncover the valve frame so that it can expand under the control of draw lines coupled to it.

The delivery catheter may further incorporate a release wire or release line which has a proximal and a distal end and which may pass through one or more lumens (channels) 864 of the multi-lumen catheter 804. The sleeve may have an aperture 868 to allow passage of such release wire or release line from a lumen of the multi-lumen catheter 804 to the exterior of the sleeve 806.

In some embodiments, slotted ring 828, having slots 870, is configured to tether or restrain the distal end of each draw line of the plurality of draw lines coming out of an aperture of the plurality of the apertures near the distal end of the sleeve and. In an example of such embodiment, shown in FIG. 9A (perspective view) and in FIG. 9B (close-up 2-dimensional view), each draw line 934 passes through a unique sleeve aperture 966 near the distal end of sleeve 906, through a distal aperture 978 in a valve frame, along a strut 976 of the valve frame 930, through a proximal aperture 974 in the valve frame 930, and between a slot 970 on the slotted ring 928. Each draw line 934 is secured in a gap 980 between ring element 928 and sleeve body 906 by the release wire or release line 972. The proximal end of the release line 972 is coupled to the gimbal handle and its distal end exits via aperture 968, may be loose or temporarily secured to sleeve 906. In some embodiments, a distal portion of release line 972 is stabilized and stays in slot 980 by the tension inserted by the plurality of the draw lines. Positioned in slot 980, release line 972 is shielded in gaps between ring elements 928 and sleeve 906. In some embodiments the distal end of release line 972 passes through aperture 968 and back into a lumen (channel) 864 of the multi-lumen catheter 804 where it is shielded within the lumen.

The draw lines may be composed of a mono filament or a plurality of filaments. The plurality of draw lines pass from the gimbal handle into and through the multi lumen tube. In one embodiment, each draw line passes into and through a unique lumen in the multi lumen tube. In some embodiments, the plurality of draw lines includes at least three draw lines. In some embodiments, the plurality of draw lines includes 3, 4, 5, 6, 7, 8, 9, 10, 11, 12, 13, 14, 15, 16, 17, 18, 19 or 20 draw lines.

In one preferred embodiment, the draw lines are comprised of a plurality of filaments and the release wire or line passes between filaments, thereby securing the draw line until the release wire or line is pulled out from between the filaments (see also, U.S. Application publication No. 2016/0331566 A1). In the example shown in FIG. 9B, draw line 934 is connected to the release wire via a gap between filaments, e.g., loop 982, formed near the distal end of draw line 934, where the gap between filaments (loop 982) may be secured with a series of knots 984 closer to the distal end of draw line 934. For single ended draw lines, there is no need for such knots in the distal end.

In yet another embodiment, the draw lines are comprised of a plurality of single-ended draw lines, each single ended draw line having a loop formed therethrough and the release line being adapted to pass through the loops of the single-ended draw lines, thereby securing the draw line until the release wire or line is pulled out from between the filaments. (see also, U.S. Application publication No. 2018/0207010 A1).

The connection between the release line and the draw lines, the function of the release line/wire and its application in transcatheter detachment of a stent from a delivery device are described in U.S. Application No. 2016/0331566A1 (based on draw lines with braided suture coupled to the release line/wire via a gap formed between filaments and secured with knots), and in U.S. Application No. 2018/0207010 A1 (based on single-ended draw lines with loops).

When the expandable transcatheter valve is to be released from the delivery system (more specifically form the sleeve 906), the proximal end of the release wire or release line 972 (that is accessible through the gimbal handle), is pulled to release the valve from the catheter, thereby releasing the draw lines from the ring element.

Figure 9B:
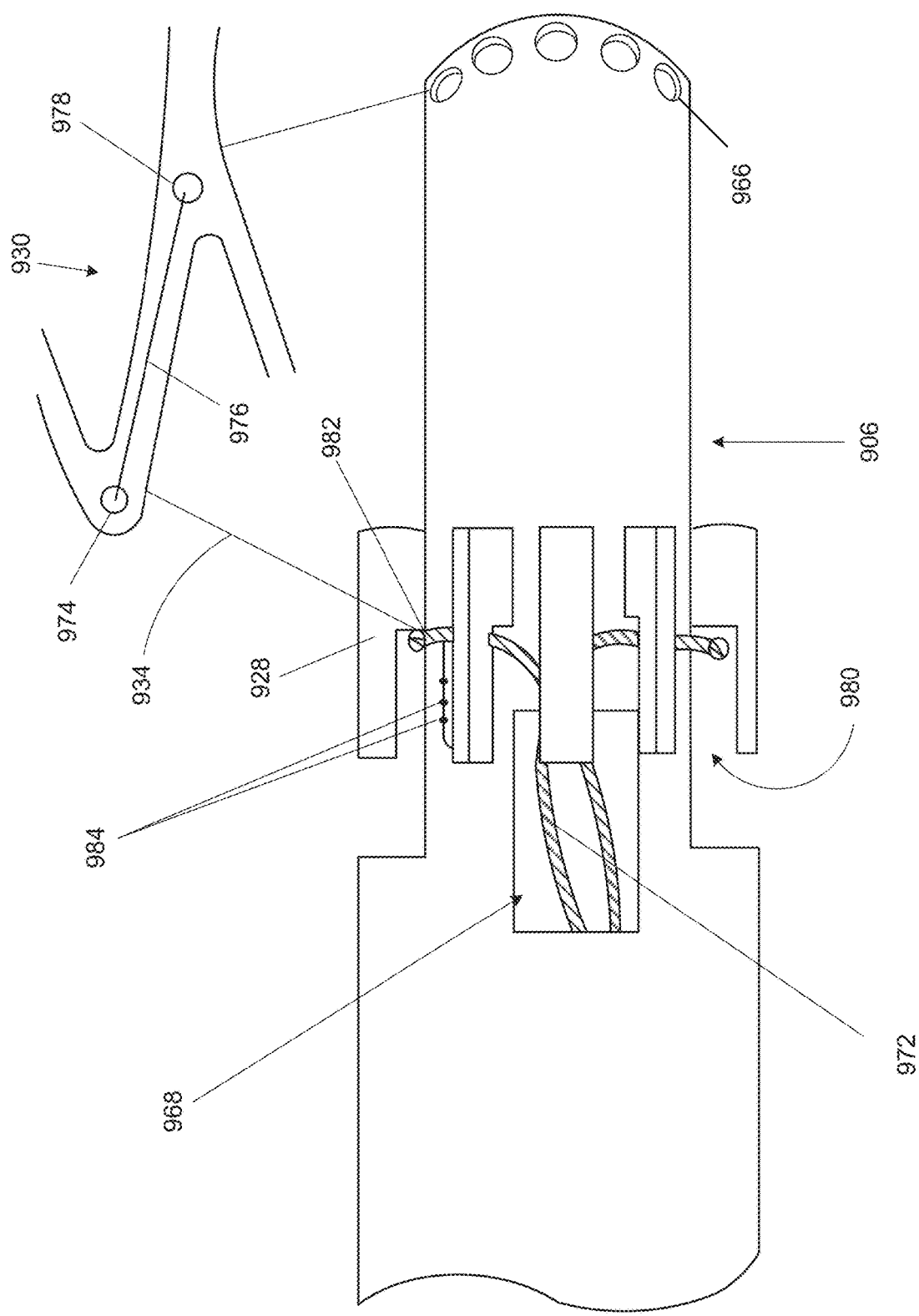
FIG. 9B. A close-up view of the example shown in part-A illustrating the connection between the valve frame and the sleeve, wherein the release wire/line passes through gaps formed between filaments of each draw line secured by a few knots.

Advantageously, the configuration shown in FIG. 9B and described above, and in particular the slotted ring element 928 attached to sleeve 906, enable the usage of thicker release wires (only limited by the size of the gap 980). Additionally, the ring element enables connection between the release line and the plurality of draw lines to be made outside of the sleeve 906, such that there is more space available in the inside of the sleeve for movement of additional elements such as an imaging catheter with an imaging probe. Moreover, such configuration enables faster and easier assembly by facilitating the placement of the release wire and its coupling to the draw lines.

In some embodiments, the sleeve 906 may include a plurality of channels inside through which the draw lines can pass. In these embodiments the number of channels in the sleeve may be equal to the number of lumens in the multi-lumen catheter 904.

Figure 9C:
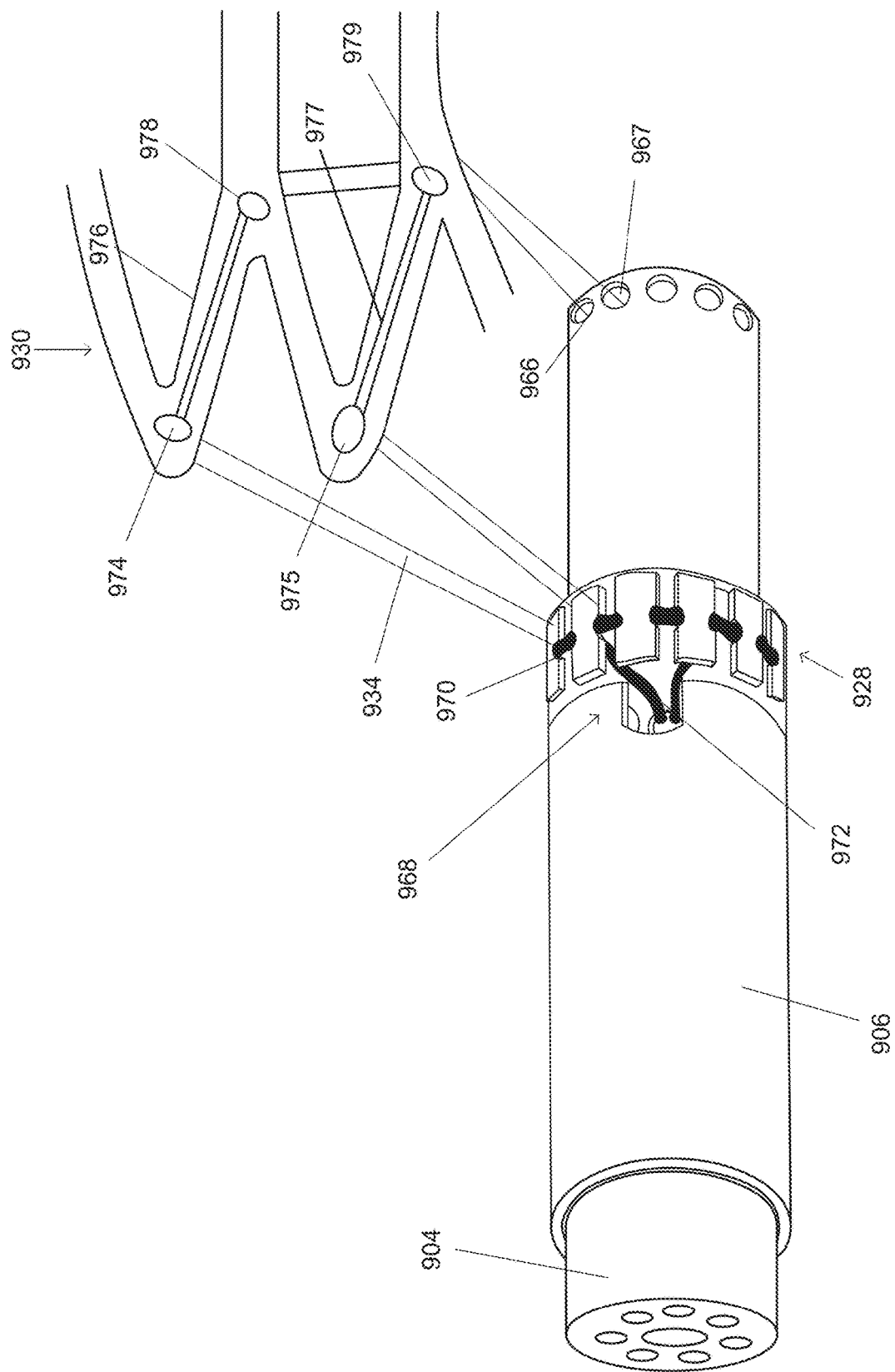
FIG. 9C illustrates an example of a sleeve coupled to a valve frame, wherein the draw lines, release line and the valve frame are coupled based on a looped stringing configuration.

Referring to FIG. 9C, in another preferred embodiment, each draw line 934 loops around the release wire or release line 972, back between a first slot 970 on the slotted ring 928, back through the proximal aperture 974 in the valve frame 930, back along the strut 976 of the valve frame 930, back through the distal aperture 978 in the valve frame 930, over to and through a second distal aperture 979 in the valve frame 930, along a second strut 977 of the valve frame 930, through a second proximal aperture 975 in the valve frame 930, between a second slot 971 on the slotted ring, around the release wire or release line 972, back between a second slot 971 on the slotted ring 928, back through the second proximal aperture 975 in the valve frame, back along the second strut 977, back through the second distal aperture 979 in the valve frame, through a second aperture 967 in the sleeve 906, through the internal space of the sleeve (or in some examples, through a channels inside the sleeve), through a second lumen in the multi-lumen catheter 904, and to a second position on the handle adjacent the other end of the draw line.

Manipulating the Valve Frame Using the Gimbal Handle

In some embodiments, the delivery system comprises the gimbal handle assembly, the multi-lumen catheter and the sleeve described above. In these embodiments, the control over plurality of draw lines, mechanically coupling the spool of the gimbal handle assembly to the valve frame, provided by the rolling, pitching or yawing the spool, may enable precise orientation and positioning of valve frame with respect to the a cavity inside a body (e.g., the aortic annulus), where the valve has to be implanted. Some embodiments may enable stepwise deployment of the valve as well as repositioning in the radial or lateral (e.g., towards the aortic wall and axial direction (e.g., towards the left ventricle (LV) or the ascending aorta).

Using the gimbal handle to swivel through various positions, as depicted in FIG. 7, (A)-(D), the handle gimbals and spool are tilted, causing selective tightening and releasing of the draw lines corresponding to the position of the draw lines around the gimbal, which causes a corresponding change in the tilt (pitch and yaw) and/or lateral movement of an attached expanding valve with respect to the sleeve.

The gimbal handle may be used to change the pitch and/or yaw of an attached expanding valve by up to ±180°, including the following exemplary values there-between: −175°, −170°, −165°, −160°, −155°, −150°, −145°, −140°, −135°, −130°, −125°, −120°, −115°, −110°, −105°, −100°, −95°, −90°, −85°, −80°, −75°, −70°, −65°, −60°, −55°, −50°, −45°, −40°, −35°, −30°, −25°, −20°, −15°, −10°, −5°, 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, and 175°.

The gimbal handle may be used to roll the attached expanding valve by up to 360°, including the following exemplary values: 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, 180°, 185°, 190°, 195°, 200°, 205°, 210°, 215°, 220°, 225°, 230°, 235°, 240°, 245°, 250°, 255°, 260°, 265°, 270°, 275°, 280°, 285°, 290°, 295°, 300°, 305°, 310°, 315°, 320°, 325°, 330°, 335°, 340°, 345°, 350°, 355° and 360°.

In some embodiments, the gimbal handle spool can be rotated in a first direction to retract the plurality of draw lines and cause the valve frame to contract, and in a second direction opposite to the first direction to allow the valve frame to expand.

In other embodiments, the gimbal handle spool can be rotated in a first direction to retract the plurality of draw lines and cause the valve frame to contract from a fully expanded state to a collapsed state, and in a second direction opposite to the first direction to release the plurality of draw lines and allow the valve frame to expand from a collapsed state to a fully expanded state.

Self-expanding transcatheter heart valves and delivery, repositioning and/or percutaneous retrieval of the transcatheter heart valves are described in U.S. Application No. 2014/0277414 and U.S. Pat. No. 9,744,037.

Examples of delivery devices for repositioning and/or percutaneous retrieval of percutaneously implanted heart valves, including a medical device handle that enable radial expansion or contraction and/or lateral positioning control over the heart valve during the medical procedure are described in U.S. Pat. Nos. 9,744,037 and 9,668,859 B2.

Advantageously, the gimbal handle assembly provides additional degrees of freedom and more fine-tuned precision with regard to the position and orientation of the valve frame during implantation in a manner not previously disclosed or enabled by prior development. Importantly, for example, in some embodiments the gimbal assembly allows tilting and laterally moving the valve frame while the valve frame is not fully expanded (i.e., in a semi-expanded state).

In some preferred embodiments, the sleeve is coupled only to the proximal end of the valve frame. Examples of such embodiments are shown in FIGS. 9A, 9B and 9C. In these embodiments, for any given level of tension on the draw lines, induced by adjusting the rotational state of the spool, the proximal end of the valve frame, that is directly coupled to the draw lines is more contracted than its distal end that is indirectly coupled the draw lines (via a network of struts). In some such embodiment, the maximum tile and angle of the valve, with the respect to the sleeve, is limited by the level of contraction of the proximal end.

Figure 10:
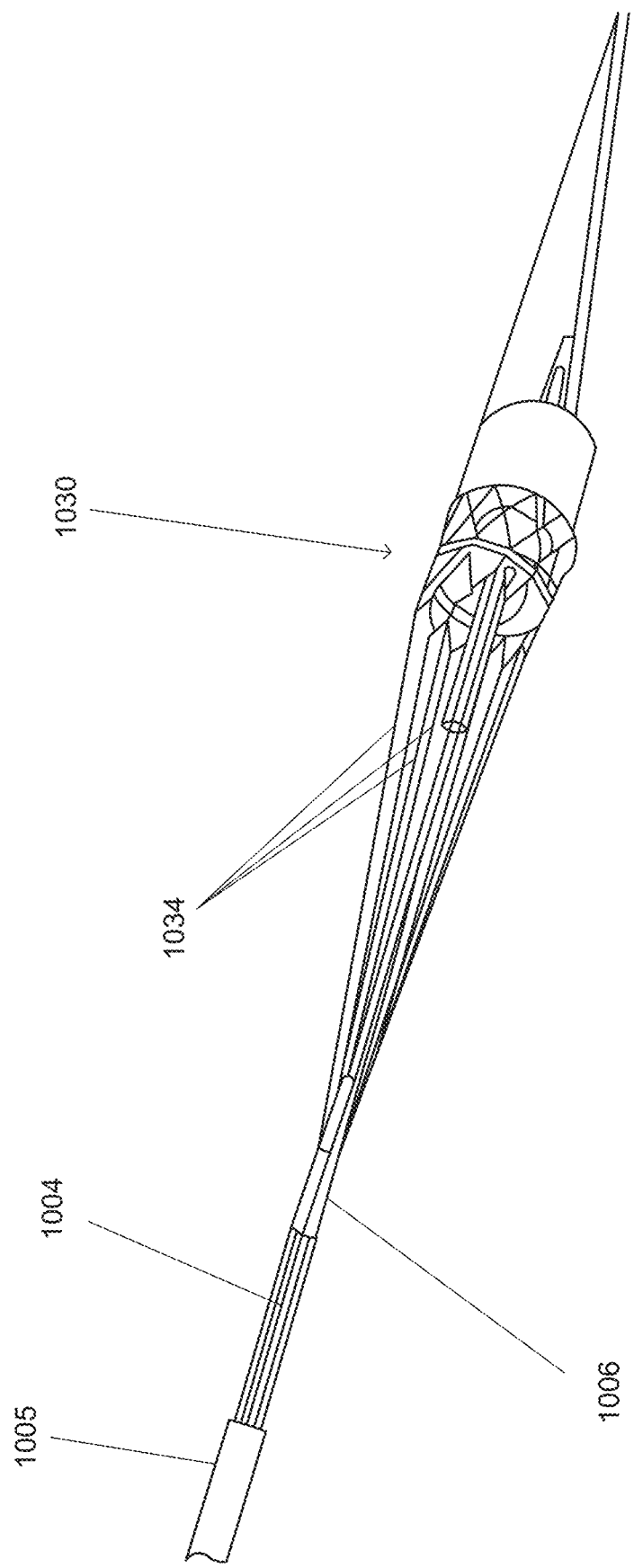
FIG. 10. A photograph showing the loading process, wherein a transcatheter heart valve is coupled to the sleeve using several draw lines.

FIG. 10 shows the loading process wherein a transcatheter heart valve 1030 is coupled to the sleeve 1006 of a transcatheter delivery system using several draw lines 1034. The sleeve 1006 is connected to a multi-lumen catheter 1004 and the catheter sheath 1005 is pulled back to provide access to the sleeve 1006 during loading process. The heart valve 1030, is kept in fully expanded state and away from the sleeve 1006 to facilitate the loading process (i.e., attachment of the draw lines 1034 to the sleeve 1006 and the heart valve 1030).

Imaging Systems

In addition, the delivery system architecture may incorporate a visualization system for image-directed heart valve delivery. These embodiments involve a catheter or catheter-like device that utilizes an integrated imaging modality with a deployment mechanism. As such, these embodiments may be used to accurately deploy a heart valve into a patient with great accuracy and precision. An imaging system allows the user to observe an image of the internal channel of a body through which the catheter passes (e.g., a vein or artery) and a cavity or channel of a body in which the valve is to be implanted.

In these embodiments, the delivery system incorporates a catheter-based imaging modality within the device, such as, but not limited to, intravascular ultrasound (IVUS), intravascular photoacoustic (IVP A) imaging, optical coherence tomography (OCT), an optoelectronic system or a fiber-optic system, raman spectroscopy, or an optical method, capable of detecting features of a vessel in which the catheter is inserted. The selected imaging systems allow clinicians to image both the surrounding anatomy and the advancing catheter in real-time during the procedure. In these embodiments, the image sensor or the imaging head may be attached or secured to the distal end of the sleeve and the image or signal transfer cable (i.e., optical fiber, BNC cable, and the like) passes through the handle, through a lumen of the delivery catheter system, through the sleeve, through the valve frame and valve, and is connected (e.g., optically or electronically) to the image sensor or imaging head. The imaging system may be used independent of the delivery catheter.

In one example, since IVUS is a tomographic imaging modality, a 3D image of the aortic root can be produced through pull-back imaging. High-resolution IVUS is well known for interrogating the lumen wall of vessels and has also been used to visualize metal stents in vivo. In the example of IVUS hardware, a physician can accurately image and position the implantable valve device without the use of ionizing radiation or nephrotoxic contrast agents. Furthermore, IVUS advantageously provides for a real-time imaging modality.

A catheter system can be based upon an imaging catheter or a valve delivery catheter. In an embodiment where the catheter system is based upon the valve delivery catheter, the imaging modality device can be inserted through the center of the valve delivery catheter, where the active imaging element is aligned with a feature of the valve delivery catheter, such as, but not limited to the catheter tip, the distal or proximal end of the valve stent, or some other predetermined landmark of the valve delivery catheter.

Positioning of the imaging device on the circumference of the valve delivery catheter is also possible in another embodiment to prevent visual hindrance from the implanted stent.

Operation of the delivery system allows visualization of the surrounding anatomy during insertion of the imaging catheter in the context of the location of the delivery catheter. As such, the location of the delivery catheter relative to the surrounding environment may always be known. In one embodiment, the delivery system is fixed relative to the imaging transducer within the catheter. In another embodiment, the two components can be moved relative to one another, wherein an imaging catheter having an associated imaging probe can be moved throughout the multi-lumen catheter before, during and after implantation of a heart valve, for example. An imaging catheter may be configured to have an internal lumen having an internal diameter that can accommodate a guide wire so that the imaging catheter can slide forward and backwards on the guide wire. However, in embodiments where relative motion is allowed, the relative motion is advantageously tracked or known in order to maintain accuracy in the advancing catheter.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A transcatheter valve delivery assembly comprising:
    a gimbal handle assembly comprising an elongate member, an inner gimbal and an outer gimbal disposed around the elongate member, and a spool coupled to and rotatable around the outer gimbal, wherein the outer gimbal is coupled to the inner gimbal by a first rotatable joint, and the inner gimbal is coupled to the elongate member by a second rotatable joint, wherein the rotatable joints allow for rotational tilting of the outer gimbal and spool with respect to a longitudinal axis of the elongate member, the rotational tilting comprises pitch movement, yaw movement, and roll movement;
    a multi-lumen catheter, its proximal end being operably linked to the elongate member of the gimbal handle assembly; and
    a plurality of draw lines, wherein proximal ends of the draw lines are attached to the spool of the gimbal handle assembly in a circumferential configuration, wherein the draw lines pass through or around both the outer gimbal and inner gimbal via apertures or channels to and through the elongate member and further through the catheter and exiting therefrom, and distal ends of the draw lines are available to be attached to a valve frame, wherein tension and position of the distal ends of the draw lines can be controlled by changing a rotational state of the spool.

2. The transcatheter valve delivery assembly according to claim 1, wherein
    rotation of the spool and the outer gimbal around the first rotational joint introduces differential increases in tension of some of the plurality of draw lines and differential reduction in tension of other of the plurality of draw lines, thereby rotating an object circumferentially connected to distal ends of the plurality of draw lines around a first axis, and rotation of the spool, outer gimbal and inner gimbal around the second rotatable joint introduces differential increases in tension of some of the plurality of draw lines and differential reduction in tension of other of the plurality of draw lines, thereby rotating the object circumferentially connected to distal ends of the plurality of draw lines around a second axis that is orthogonal to the first axis.

3. The transcatheter valve delivery assembly according to claim 2, wherein tilt angles of the spool/outer gimbal relative to the longitudinal axis of the elongate member may be changed by up to ±60° upon rotation of the spool and outer gimbal around the longitudinal axis of the elongate member.

4. The transcatheter valve delivery assembly according to claim 1, wherein the plurality of draw lines comprises at least three draw lines.

5. The transcatheter valve delivery assembly according to claim 1, further comprising a slide lock that locks the inner gimbal, the outer gimbal and the elongate member together in a neutral position, wherein none of the gimbals or the spool can tilt in any direction with respect to the longitudinal axis of the elongate member, but the spool can rotate around the outer gimbal, wherein rotation of the spool around the outer gimbal uniformly increases or decreases tension in the plurality of draw lines.

6. The transcatheter valve delivery assembly according to claim 1, further comprising:
 a sleeve attached to a distal end of the multi-lumen catheter,
 wherein the gimbal handle assembly is operably linked to the multi-lumen catheter and the sleeve and wherein a transcatheter valve frame of the transcatheter valve delivery assembly is operably linked to the gimbal handle assembly through the multi-lumen catheter and sleeve by the plurality of draw lines.

7. The transcatheter valve delivery assembly according to claim 6, further comprising a catheter sheath that is capable of being slid along the longitudinal axis of the sleeve, wherein the catheter sheath may cover the transcatheter valve in a first position, thereby holding the transcatheter valve in a contracted position, or the catheter sheath may be withdrawn to a second position wherein the transcatheter valve is partially or completely exposed, thereby permitting the transcatheter valve to partially or completely expand.

8. The transcatheter valve delivery assembly according to claim 7, further comprising a rotatable coupler that can be used to either tighten and secure or release a proximal end of the catheter sheath, to allow pushing or pulling of the catheter sheath to cover or uncover the sleeve.

9. The transcatheter valve delivery system according to claim 6, further comprising a release wire or release line that passes through the gimbal handle assembly and through the multi-lumen catheter, wherein a distal end of the release wire or release line passes through an aperture in the sleeve to the exterior of the sleeve and wraps around a circumference of the exterior of the sleeve.

10. The transcatheter valve delivery assembly according to claim 9, wherein the multi-lumen catheter comprises a slotted ring affixed externally around the sleeve, wherein distal ends of each of the plurality of draw lines engage the release wire or release line within the slotted ring, wherein pulling and withdrawal of the release wire or release line from its proximal end decouples the draw lines from the release wire or release line.

11. The transcatheter valve delivery assembly according to claim 9, wherein a distal portion of the release wire or release line is shielded in gaps between the sleeve and wherein the distal end of the release wire or release line passes back through the sleeve and into the multi-lumen catheter.

12. The transcatheter valve delivery assembly according to claim 9, wherein distal ends of each of the draw lines are removably attached to the release wire or release line.

13. The transcatheter valve delivery assembly according to claim 1, further comprising an imaging catheter that comprises an imaging probe at a distal end, wherein the imaging catheter is configured to pass through the gimbal handle assembly, and the multi-lumen catheter.

14. The transcatheter valve delivery assembly according to claim 1, wherein the valve is a heart valve.

\* \* \* \* \*